US007767397B2

(12) United States Patent
Fischer

(10) Patent No.: US 7,767,397 B2
(45) Date of Patent: Aug. 3, 2010

(54) HEPOXILINS AND MODULATORS OF ICHTHYIN FOR TREATMENT SKIN DISORDERS

(75) Inventor: Judith Fischer, Paris (FR)

(73) Assignee: Consortium National de Recherche en Genomique Composante Centre National de Genotypage (C.N.R.G.), Evry Cedex (FR)

( * ) Notice: Subject to any disclaimer, the term of this patent is extended or adjusted under 35 U.S.C. 154(b) by 21 days.

(21) Appl. No.: 11/597,840

(22) PCT Filed: Jun. 3, 2005

(86) PCT No.: PCT/IB2005/001763

§ 371 (c)(1),
(2), (4) Date: Nov. 29, 2006

(87) PCT Pub. No.: WO2005/117897

PCT Pub. Date: Dec. 15, 2005

(65) Prior Publication Data

US 2007/0197639 A1    Aug. 23, 2007

(30) Foreign Application Priority Data

Jun. 3, 2004    (EP) .................................. 04291387

(51) Int. Cl.
*C12Q 1/68* (2006.01)
*C12P 19/34* (2006.01)
(52) U.S. Cl. ........................... 435/6; 435/91.1; 435/91.2
(58) Field of Classification Search ........................ None
See application file for complete search history.

(56) References Cited

FOREIGN PATENT DOCUMENTS

| WO | 97/29751 | 8/1997 |
| WO | 02/38157 A2 | 5/2002 |
| WO | 2004/104022 A2 | 5/2004 |

OTHER PUBLICATIONS

Halushka, et al. Nature Genetics, 1999; 22:239-247.*
Krebsova, et al. Am. J. Hum. Genet. 2001; 69:216-222.*
Moller, et al. Neuroscience Letters, Apr. 15, 2004; 359(3): 195-197.*
Hirschhorn et al. Genetics in Medicine. vol. 4, No. 2, pp. 45-61, Mar. 2002.*
Ioannidis. Nature Genetics, vol. 29, pp. 306-309, Nov. 2001.*
GenBank dbSNP Accession No. rs1105282, NCBI Assay ID ss4920029 Entry Date Jul. 24, 2002; URL: http://www.ncbi.nlm.nih.gov/SNP/snp_ref.cgi?rs=1105282 and Assay ID ss4920029 method URL: http://www.ncbi.nlm.nih.gov/SNP/snp_viewTable.cgi?mid=604.*
GenBank record AY399354, Dec. 12, 2003, GI: 39755343, Homo sapiens HCM0196 gene, pp. 1-2.*
Vieland et al. Human Heredity, 2001, vol. 51,pp. 199-208.*
Zhao et al. Journal of Investigative Dermatology (2007) 127, 1878-1882.*
Stone et al, "Missense Variations in the Fibulin 5 Gene and Age-Related Macular Degeneration", N. Engl. J. Med., Jul. 22, 2004, vol. 351, No. 4; pp. 346-353.
Fischer et al, "The gene encoding adipose triglyceride lipase (*PNPLA2*) is mutated in neutral lipid storage disease with myopathy", Nature Genetics, Jan. 2007, vol. 39, No. 1, pp. 28-30.
Loeys et al, "Human Molecular Genetics", Hum. Mol. Genet. 2002, vol. 11, pp. 2113-2118.
Schoenborn et al, "The *ATGL* Gene Is Associated With Free Fatty Acids, Triglycerides, and Type 2 Diabetes", Diabetes, May 2006, vol. 55, No. 5, pp. 1270-1275.
Dahlqvist et al, "Congenital ichthyosis: mutations in ichthyin are associated with specific structural abnormalities in the granular layer of epidermis", 2007, J Med Genet, 44, 615-620.
Eckl et al, W8 01, Medgen 18 (2006) "Mutations in the gene for ichthyin in patients with autosomal recessive congenital ichthyosis—disease causing or polymorphic?".
Gehris et al, "Clinical and Molecular Diagnosis of Congenital Ichthyosis and Related Disorders" Forum 509, AAD Aug. 2007, Neonatal and Infantile Dermatology, pp. 1-9.
"Genetic Testing of the *ALOX12B, ALOXE3* and *Ichthyin* Genes in Congenital Recessive Ichthyosis" GeneDx, Inc., GeneDx Revision Date: Apr. 2008, pp. 1 and 2).
Bale et al, "Autosomal Recessive Congenital Ichthyosis", GeneReviews, 2008, pp. 1-17.
Wang et al, "*Drosophila* spichthyin inhibits BMP signaling and regulates synaptic growth and axonal microtubules", Nature Neuroscience, 2007, 10(2):177-85.
International Search Report of PCT/IB2005/001763, mailed Jan. 12, 2006.
Anton et al; "Occurrence of Hepoxilins and Trioxilins in Psoriactic Lesions", The Journal of Investigative Dermatology, vol. 110, No. 4, Apr. 1998, pp. 303-310, XP000961695.
Pace-Asciak et al., "The Hepoxilins", Advances in Experimental Medicine and Biology, vol. 447, Apr. 1, 1999, pp. 123-132, XP008003970.
Lefevre et al., "Mutations in ichthyin a new gene on chromosome 5q33 in a new form of autosomal recessive congenital ichthyosis", Human Molecular Genetics, 2004, vol. 13, No. 20, Oct. 15, 2004, pp. 2473-2482, XP002326350.

* cited by examiner

*Primary Examiner*—Juliet C Switzer
(74) *Attorney, Agent, or Firm*—Nixon & Vanderhye P.C.

(57) ABSTRACT

The present application relates to compositions and methods for treating skin disorders, dry skin, and protection of skin in inflammatory events. The present application more particularly discloses the identification of new genes and metabolic pathways involved in skin disorders, which provide novel targets and approaches for treating said disorders and for screening biologically active compounds. The present invention also provides various products and constructs, such as probes, primers, vectors, recombinant cells, which can be used to implement the above methods. The invention may be used to detect or treat various skin disorders, particularly dry and inflammatory skin disorders, in various subjects, including mammalian subjects, particularly human beings.

3 Claims, 7 Drawing Sheets

FIGURE 2

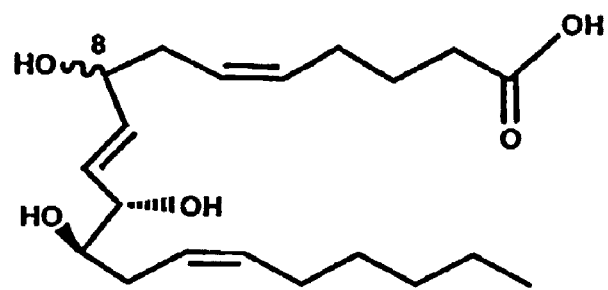
12-(R)-TXA-3
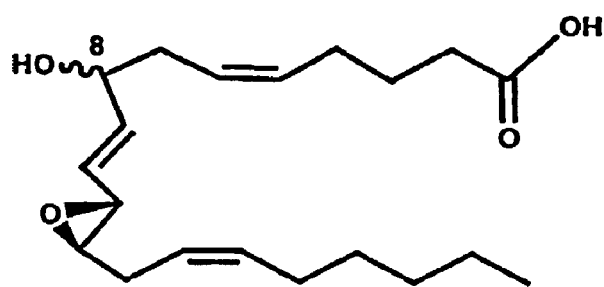
12-(R)-HXA-3
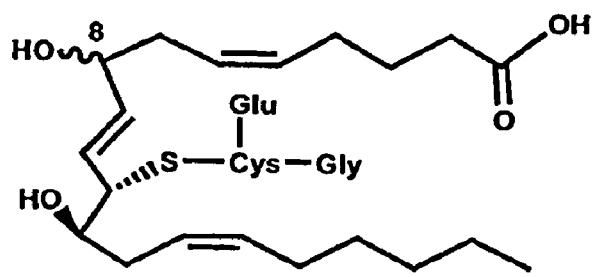
12-(R)-HXA-3-C
Figure 3 A

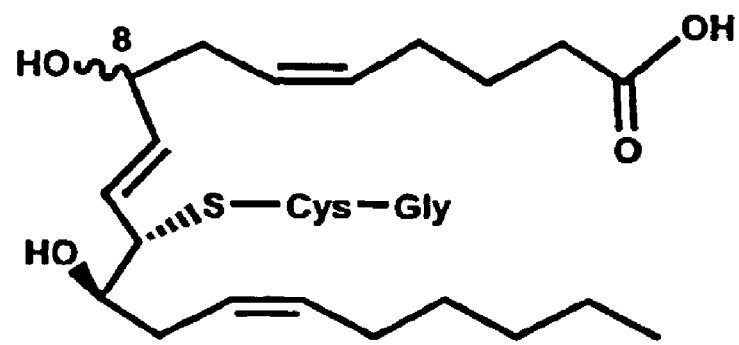
12-(R)-HXA-3-D
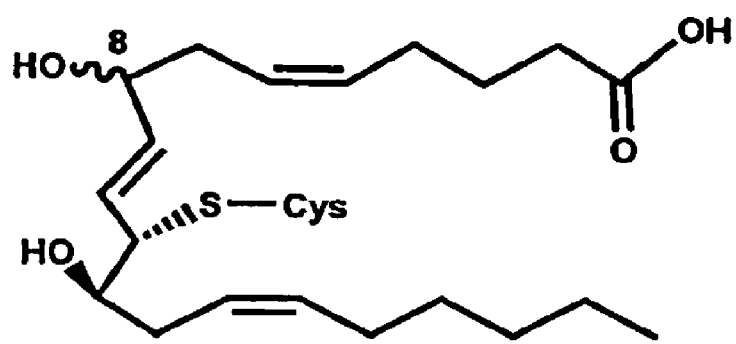
12-(R)-HXA-3-E
Figure 3B

```
atggagctgc gggtcagcaa caccagctgc gagaacggtt ccctgctcca cctctactgc   60
tcctcccaag aagtcctgtg ccagattgtc aatgacctca gccctgaggt gcccagcaat  120
gccacctttc acagctggca ggaaagaatc aggcagaact atggcttcta catcggcctg  180
ggcctggcat tcctgtctag cttcctcatc ggcagcagcg tcatcctcaa gaagaaaggc  240
ctcttgcgac tcgtggccac gggagccact cgagctgtgg atggaggctt cggctacctg  300
aaagatgcaa tgtggtgggc tggatttctc accatggctg ctggagaagt tgccaacttt  360
ggagcctacg catttgcacc tgcaacagtc gtcacgcctc tgggagcgct gagtgtcctc  420
ataagtgcca tcctctcctc atatttcctg agggagagtc tgaacctgct ggggaagctg  480
ggctgtgtga tctgtgtggc cggaagcaca gtgatggtga tacatgctcc tgaggaagag  540
aaggtcacta ccatcatgga gatggcttcc aagatgaaag acacagggtt catcgtgttt  600
gctgtgcttc tgctggtgtc atgcctcatc ctcatctttg tcattgcccc acgttacggg  660
caaaggaata tcctcatcta catcatcatc tgctctgtga tcggggcctt ctctgtggct  720
gctgtcaagg gctgggcat caccatcaag aacttcttcc agggctgcc agttgtccgg  780
cacccgctcc cctacatcct gtccctcatc ctggcactgt ccctcagcac tcaggtcaac  840
ttcctcaaca gagcactgga cattttcaac acttccctgg tgttccccat ctactacgtg  900
ttcttcacca cggtggtcgt tacctcgtcc atcatcctct tcaaggagtg gtacagcatg  960
tctgctgtgg acattgcagg caccctctcg ggctttgtca ccatcatctt gggcgtgttc 1020
atgctgcatg ctttcaaaga cctggacatc agctgcgcca gcttgcccca catgcacaaa 1080
aacccacccc cttctcccgc cccggaaccc actgtcatta gactggaaga caagaacgtc 1140
cttgtggaca atatagaact tgccagcacc tcatcaccag aagagaaacc caaagtattt 1200
ataatccatt cctga                                                  1215
```

Figure 4

HEPOXILINS AND MODULATORS OF ICHTHYIN FOR TREATMENT SKIN DISORDERS

This application is the US national phase of international application PCT/IB2005/001763, filed 3 Jun. 2005, which designated the U.S. and claims priority of EP 04291387.1, filed 3 Jun. 2004, the entire contents of each of which are hereby incorporated by reference.

The present application relates to compositions and methods for treating skin disorders. The present application more particularly discloses the identification of new genes and metabolic pathways involved in ichthyosis and, more generally, skin hydration and protection of skin in inflammatory events, which provide novel targets and approaches for treating said disorders and for screening biologically active compounds. The present invention also provides various products and constructs, such as probes, primers, vectors and recombinant cells, which can be used to implement the above methods. The invention may be used to detect or treat various skin disorders, particularly dry skin disorders and inflammatory events, in various subjects, including mammalian subjects, particularly human beings.

The metabolic pathways from arachidonic acid ("AA"), which lead to leukotrienes, hepoxilins and lipoxins, have been mainly defined by the biochemical identification of their numerous intermediates and products.

Leukotrienes and lipoxins are potent lipid mediators derived from AA, via activation of 5-lipoxygenase and 15-lipoxygenase enzymes. All of them belong to the large eicosanoid family of small lipid messengers generated by divergent metabolic pathways from AA, and are implicated in biological functions as diverse as chemotaxis, vascular permeability, smooth muscle contraction, inflammation, and in the pathophysiology of various inflammatory and hypersensitivity disorders such as asthma. Recent reviews have summarized the present knowledge of their metabolism, biological actions, and implication in common and rare disorders.

Another metabolic pathway, which also starts from AA but proceeds via activation of 12-lipoxygenase, leads to several trihydroxytetraene products of the hepoxilin family (acronym for hydroxy epoxid with a biological activity in insulin secretion). Hepoxilin and other intermediates or products act primarily on calcium and potassium channels in membranes, which ultimately result in a wide range of functions including insulin secretion, vascular permeability, vasoconstriction, synaptic transmission, cell volume regulation, and activation of neutrophils and platelets. However, paradoxically, this pathway has received less attention since its discovery during the eighties.

Based on the identification of several genes implicated in a group of rare dermatological disorders (15-20), the autosomal recessive congenital ichthyoses (ARCI), the present inventors now disclose a novel metabolic pathway leading to hepoxilin with 12(R)-chirality, as well as its unexpected and undisclosed implication in skin disorders. The present application thus discloses novel genes, metabolites, targets and therapeutic approaches to the treatment or prevention of particular skin conditions.

More particularly, the present invention reports the genomic localization and the identification of a gene, named ICHTHYIN, for a new form of non-syndromic autosomal recessive congenital ichthyosis (ARCI). Six homozygous mutations, including one nonsense and five missense mutations, were identified in said gene in 23 patients from 14 consanguineous families from Algeria, Colombia, Syria and Turkey. ICHTHYIN encodes a protein with several transmembrane domains which belongs to a new family of proteins localized in membranes (PFAM: DUF803), with weak homologies to both transporters and G-protein coupled receptors (GPCR).

Based on the results presented here, it is postulated that ICHTHYIN is the key membrane receptor for 12(R)-A3 trioxilin from the hepoxilin pathway. For the first time, the present application discloses the implication of the 12(R)-hepoxilin metabolic pathway in skin disorders. The present inventors also propose, for the first time, a function of particular genes in the 12(R)-hepoxilin metabolic pathway.

A particular object of this invention thus resides in a method of detecting, diagnosing or characterizing the presence of, or predisposition to a skin disorder in a subject, comprising assessing, in a biological sample from said subject, the presence of a genetic alteration in the ICHTHYIN gene or corresponding protein, the presence of a genetic alteration in said gene or protein being indicative of the presence of or predisposition to a skin disorder in said subject.

As will be disclosed further below, the genetic alteration may be a mutation, a deletion, an insertion, a splice site mutation, an inversion, an addition and/or a substitution of one or more residues in said gene or encoded protein, typically a mutation. The biological sample may be any tissue, cell or fluid that contains an ICHTHYIN gene or polypeptide, preferably a sample comprising genomic DNA from the subject.

A further aspect of this invention resides in nucleic acid probes and primers that can specifically hybridise to or amplify all or a distinctive part of the ICHTHYIN gene.

A further aspect of this invention is a method of amplifying an ICHTHYIN gene, the method comprising:
(i) providing a biological sample containing an ICHTHYIN gene or a portion thereof,
(ii) contacting said sample with (a pair of) primers as defined above, and
(iii) amplifying the ICHTHYIN gene or mRNA.

Another object of this invention is a method of selecting or identifying biologically active compounds, comprising contacting a candidate compound with an ICHTHYIN protein or a related receptor, and determining whether said compound binds to or modulate the activity of said protein. In a particular embodiment, the method comprises contacting the test compound with a recombinant host cell expressing an ICHTHYIN protein or a related protein, and selecting the compounds that bind said protein or modulate its activity.

A further object of this invention is a recombinant host cell comprising a genetic construct encoding an ICHTHYIN protein or a related protein, said cell expressing said protein as a membrane protein. The recombinant cell of this invention may be a prokaryotic or eukaryotic cell. It may be a primary cell or an established cell line, of various origins.

Still a further aspect of this invention resides in an antibody that specifically binds an ICHTHYIN protein or a related protein.

An other object of this invention resides in the use of a compound selected from a metabolite of the 12(R)-hepoxilin pathway or an analog thereof (for instance, an ester derivative, an amide derivative thereof), for the manufacture of a medication (or medicament) for the treatment of a skin disorder, as well as in a corresponding method of treatment. The compound may be selected, for instance, from 12(R)-TXA3, 12(R)-HXA3, 12(R)-HXA3-C, 12(R)-HXA3-D and 12(R)-HXA3-E, as well as any ligand of an ICHTHYIN protein, particularly 12(R)-TXA3 or an agonist or synthetic analog thereof. Those compounds may be prepared in vitro from arachidonic acid using native or recombinant12R-lipoxygenase encoded by human ALOX12B gene, 12R-epoxide isomerase encoded by human ALOXE3 gene, an epoxide hydrolase, or a glutathione S-transferase, a glutamyl transpeptidase, a dipeptidase, or combinations of those enzymes (FIG. 5). Synthetic methods for the preparation of racemic HXA3 have also been reported (39-40).

An other object of this invention is a composition comprising a metabolite of the 12(R)-hepoxilin pathway, or an analog thereof, and a pharmaceutically acceptable carrier, preferably for topical application.

Still another object of this invention are metabolites of the 12R-hepoxilin pathway such as 12(R)-TXA3, 12(R)-HXA3-C, 12(R)-HXA3-D and 12(R)-HXA3-E, and their ester or amide derivatives, usefull for the treatment of dry skin.

The invention may be used to detect, diagnose, classify, treat (including prevention of) a skin disorder in a subject, particularly a dry skin disorder, notably dermatosis, such as atopic skin, contact dermatitis, eczema, psoriasis, or a keratinization disorder such as an ichthyosis and a palmoplantar keratoderma, or to protect skin in inflammatory events; or to screen, identify, select or produce compounds for use in treating or preventing a skin disorder.

Definitions

Dry skin disorders: Within the context of the present invention, a "dry skin" disorder refers generally to any pathology associated with or resulting from an impaired skin barrier function and/or with epidermis dryness. Dryness and skin barrier disorders are not a single entity, but are characterized by differences in chemistry and morphology in the epidermis. (38). Specific examples of such diseases or disorders include atopic skin, contact dermatitis, eczema, psoriasis and keratinisation disorders such as ichthyosis. Skin disorders also include skin inflammation as well as skin affections resulting from various type of aggressions, including chemical (acid, sodium hydroxide, etc.), physical (e.g., X-ray, UV, etc.), or biological (e.g., infections) aggressions.

ICHTHYIN gene: Within the context of the present invention, the term ICHTHYIN gene refers to a nucleic acid molecule having a sequence as disclosed in FIG. 4 (SEQ ID No: 1), encoding a receptor for a ligand of the hepoxilin metabolic pathway, as well as any portion thereof, naturally occurring variant thereof, such as variants resulting from polymorphisms, splicings, etc., and orthologs thereof. The term "ICHTHYIN gene" applies to coding and non-coding parts of the genomic DNA or RNA, such as promoter, poly A, intronic sequences, etc. The term gene also includes the coding region, in the form of genomic DNA, cDNA, RNA (pre-rRNA, messenger RNA, etc), etc. or any synthetic nucleic acid comprising all or part of the sequence thereof. Synthetic nucleic acid includes cDNA, prepared from RNAs, and containing at least a portion of a sequence of the ICHTHYIN gene as for example one or more introns or a portion containing one or more mutations. Those nucleic acids can be isolated from known banks by hybridization techniques under stringent conditions at best. They can also be genetically or chemically synthesized.

The sequences of wild type human ICHTHYIN gene is available in the literature under the following accession numbers : LocusID LOC348938; mRNA AK026158 (GI: 10438919); mRNA XM_371777 (GI:42657191). The sequence of mouse ICHTHYIN gene may be found as Mus musculus RIKEN cDNA 9530066K23Rik, LocusID 214112; mRNA NM_172524 (GI:27369725) identical to AK035561 (GI:26330753). The sequence of rat ICHTHYIN gene may be found at LocusID LOC303070; mRNA XM_220330.2 (GI: 34870677).

A portion or part of a gene means at least 3 nucleotides, preferably at least 9 nucleotides, even more preferably at least 15 nucleotides, and can contain as many as 1000 nucleotides or more. Such a portion can be obtained by any technique well known in the art, e.g., enzymatic cleavage, chemical synthesis or a combination thereof. A distinctive portion of an ICHTHYIN gene refers to a fragment of at least 5, preferably at least 8 consecutive nucleotides that are specific for a sequence as disclosed above. A distinctive portion may also contain a genetic alteration, as disclosed below.

ICHTHYIN protein: Any polypeptide encoded by an ICHTHYIN gene as defined above. As a specific example, the sequence of wild type human ICHTHYIN protein is available in the literature under the following accession number: XP_371777 (GI:41146935) (SEQ ID No 2), the mouse protein is available as NP_766112 (27369726), and the rat protein is available as XP_220330.1; XP_220330.2 (GI: 34870678).

ICHTHYIN related protein: ICHTHYIN related proteins include a group of receptors, which have now been identified by the present inventors as being involved in arachidonic acid metabolic pathway, which include i) NIPA1 (Non-Imprinted in Prader-Willi/Angelman syndrome 1); ii) NIPA2 (DUF803.0); LocusID 81614; mRNA NM_030922 or BC011775 (GI:33989168); iii) LOC152519 (DUF803.3) iv) FLJ13955 (DUF803.1) LocusID 79815; NM_024759 (GI: 13376096) identical to AK024017 (GI:10436266); and v) dJ462023.2 (DUF803.4). BLAST analysis identified the above genes as human paralogs of ICHTHYIN. Among these genes, the first three are the most closely related to ICHTHYIN, with up to 57% homology. The term "ICHTHYIN related proteins" includes the above listed proteins, in their wild-type form, as well as naturally occurring variants thereof, resulting for instance from polymorphism, splicing, etc. The amino acid and nucleotide sequences of these members are available in the literature. The present invention now demonstrates that these proteins have very significant sequence homology and represent a new family of receptors involved in arachidonic acid metabolic pathway.

Identification of a Novel Gene and Metabolic Pathway Involved in Dry Skin Disorders The clinically and genetically heterogeneous group of autosomal recessive congenital ichthyoses (ARCI) is characterized by generalized desquamation of the skin, usually with erythema (1-3). Most of the patients are born as collodion babies. The disease may progress to two main clinical forms, either lamellar ichthyosis (LI) or non-bullous congenital ichthyosiform erythroderma (NCIE). The estimated incidence is between one in 300,000 to 500,000 for both forms. LI differs from NCIE in the characteristics of the scales, which are large, adherent, dark and pigmented, and in the absence of skin erythema. In NCIE, the scales are fine and white on an erythematous background, although they are larger and grayish on the limbs (3). Overlapping phenotypes have been described, and may depend on age of the patient, and the region of the body. LI is characterized histologically by ortho-hyperkeratosis and mild focal parakeratosis. Hyperkeratosis associated with an increase in stratum corneum thickness, a normal or prominent granular layer, and increased mitoses suggest a hyperproliferative epidermal defect in NCIE (3). Prominent dermal flood vessels and an upper lymphocytic infiltrate may explain the erythroderma. The terminal differentiation of the epidermis is disturbed in both forms, leading to a reduced barrier function and defects in the stratum corneum lipid composition (2-5). LI is considered to be a retention ichthyosis, in comparison with NCIE, which is more a hyperproliferative disease (5, 6).

ARCI has been shown to be genetically heterogeneous. Five genes have been localized: LI1 (MIM 242300) on chromosome 14q11; LI2 (MIM 601277) on chromosome 2q33-35; LI3 (MIM 604777) on chromosome 19p12-q12; non-lamellar, non-erythrodermic congenital ichthyosis NNCI 19p13.2-p13.1 (MIM 604781); and LI5 (MIM 606545), also known as NCIE1 (MIM 242100) on chromosome 17p13 (7-11). Four of these genes have been identified to date: transglutaminase 1 (TGM1) for LI1 (12, 13), two lipoxygenases (ALOXE3 and ALOX12B) for LI5/NCIE1 (14), and ABCA12 for LI3 (15). Another gene, CGI-58 or ABHD5 has been shown to underlie a syndromic form of NCIE2 (MIM 242100) called Chanarin-Dorfman syndrome (16).

A genome-wide scan of two large consanguineous families with three and four affected children respectively allowed us to localize a gene on chromosome 5q33. Twelve additional consanguineous families were then found to have ichthyosis linked to chromosome 5q33. By microsatellite genotyping the inventors refined the linkage interval to 2.3 Mb based on recombination events. Haplotype analysis reduced the interval to 1 Mb. Twelve candidate genes were excluded by sequencing, before the inventors identified mutations in a new gene, that the inventors name ICHTHYIN.

The identification of mutations in a new gene with several TM domains in patients affected by ARCI is a landmark in the analysis of these disorders, for which both low incidence and wide clinical and genetic heterogeneity have made it difficult to develop a classification scheme using clinical (2, 3, 6), biochemical (5, 6, 22), and ultrastructural criteria (23). It supports a metabolic origin of ARCI, which was suggested after two genes from the lipoxygenase family (ALOX12B and ALOXE3) were found to be mutated in this disorder (14). This finding was extended by the identification of ALOXE3 as a hydroperoxide isomerase (24). The phenotype of this ARCI caused by mutations in ICHTHYIN is similar to that previously described for other ARCIs, in which the majority of patients present a NCIE phenotype. Not all ARCI patients are born as collodion babies; this was the case in 9 patients from four Algerian and two Turkish families.

One of the main difficulties in the present work was the identification of the gene, which necessitated the sequencing of all the genes present in the refined interval, and a search for new genes, which were suspected only by RNA expression. A precise characterization of the structure of this gene by RT-PCR, 5' and 3'RACE was obviously required.

With its 7-9 TM domains, ICHTHYIN is clearly membrane-associated. Based on the results presented here, including the presence of mutations correlated to skin disorders, the expression profile and the genetic organization of certain metabolic pathways, it is submitted that ICHTHYIN is a membrane receptor of the hepoxilin pathway, more particularly a receptor for a ligand from the hepoxilin pathway with R-chirality, more precisely the receptor for 12(R)-trioxilin A3 (12 (R)-TXA3). This invention is landmark and provides the first description of a receptor for a hepoxilin metabolite with R-chirality, and a key of the correlation between the 12(R)-hepoxilin pathway and skin disorders.

Furthermore, the present invention now discloses that other genes found to be mutated in ichthyoses: the CGI-58 protein or abhydrolase 5 (12, 13, 16) and the transporter ABCA12 (15), also belong to the hepoxilin metabolic pathway, in which membrane arachidonic acid is transformed to hepoxilin, trioxilin and derivatives of R-chirality (25, 26).

The identification of this novel metabolic pathway, including the ICHTHYIN protein, offers strong opportunities to provide simple treatments to patients. In particular, ICHTHYIN, as well as related proteins, is easily accessible and enables the design and the synthesis of analogues, agonists and antagonists of the ligand, with high specificity and sensitivity in the ligand-receptor interactions.

Methods of Diagnosing Skin Disorders

The present invention discloses that the ICHTHYIN gene or encoded polypeptide is genetically altered in patients having (or at risk of developing) skin disorders. This gene and polypeptide thus represent valuable biomarkers, suitable for monitoring predisposition, presence or progression of a skin disorder in a subject.

In this respect, a particular object of this invention resides in a method of detecting, diagnosing or characterizing the presence of, or predisposition to a skin disorder in a subject, comprising assessing, in a biological sample from said subject, the presence of a genetic alteration in the ICHTHYIN gene or corresponding protein, the presence of a genetic alteration in said gene or protein being indicative of the presence of or predisposition to a skin disorder in said subject.

The alteration in the ICHTHYIN gene or polypeptide may be any genetic alteration, such as a mutation, a deletion, an inversion, an insertion, a splice site mutation, an addition and/or a substitution of one or more residues in said gene or encoded polypeptide. Preferred genetic alterations are mutations in a coding or non-coding region, particularly mutations in a coding region leading to a change in amino acid sequence in the encoded polypeptide, e.g., an amino acid substitution, a frameshift and/or a truncated polypeptide sequence. Specific examples of genetic alterations in the ICHTHYIN gene are disclosed in Table 1, and include a nonsense mutation and five missense mutations: 247C→T (R83X) and 239G→T (G80V) in exon 2; 341C→A (A114D) in exon 4, 437C→T (S146F) and 523C→G (H175N) in exon 5; and 703G→A (G235R) in exon 6. The numbering corresponds to the coding sequence only, starting with 1 from the A of the initiating ATG codon (corresponding to methionin) (see FIG. 4, bold characters). By reference to the sequence of accession number XM_371777, which is the reference sequence of NCBI, 1=A of the ATG corresponds to bp 106, and goes until bp 1320=A of the TGA (corresponding to a stop codon). By reference to the sequence of accession number AK026158, which is the sequenced cDNA, 1=A of the ATG corresponds to bp 107, and goes until bp 1321=A of the TGA (corresponding to a stop codon). Numbering of amino acid residues refers to XP_371777.

The presently identified mutations are situated in parts of the gene that are highly conserved between mice, rats and humans. None of these sequence variations were found in 100 normal chromosomes from a Mediterranean control population.

The methods comprise, typically, detection of the presence of a mutation in an ICHTHYIN gene or polypeptide in a biological sample from a subject. The biological sample comprises any material such as cells, a tissue, an organ, a fluid, etc or fractions thereof, which contain nucleic acids or polypeptides. Specific examples of such biological samples include white blood cells or fluids, such as blood, plasma or urine, biopsies, skin and mucosa, which may possibly be obtained by non-invasive methods or from tissue collections, if necessary. Furthermore, since the ICHTHYIN gene is found within the cells, tissues or fluids mentioned above, the sample is usually treated to render the gene available for detection or analysis. Treatment may comprise any conventional fixation technique, cell lysis (mechanical or chemical or physical), or any other conventional method used in immuno-histology or biology, for instance.

In a first variant, the present invention, provides a method of detecting the presence of an altered ICHTHYIN polypeptide. This can be determined by any suitable technique known to the skilled artisan, including by immuno-assay (ELISA, EIA, RIA, etc.). This can be made using any affinity reagent specific for an ICHTHYIN polypeptide, more preferably any antibody or fragment or derivative thereof, particularly any affinity reagent specific for an altered ICHTHYIN polypeptide. In a particular embodiment, the ICHTHYIN polypeptide is detected with an anti-ICHTHYIN antibody (or a fragment thereof), more preferably a monoclonal antibody, as described above. The antibody (or affinity reagent) may be labeled by any suitable method (radioactivity, fluorescence, enzymatic, chemical, etc). Alternatively, ICHTHYIN-antibody immune complexes may be revealed (and/or quantified) using a second reagent (e.g., antibody), labelled, that binds to the anti-ICHTHYIN antibody, for instance.

In a second variant of the present invention, the presence of an altered ICHTHYIN gene is detected. This can be done using various techniques, as described below.

In a particular embodiment, the method comprises the characterization of all or part of an ICHTHYIN gene in the sample and the comparison of said gene to the wild-type ICHTHYIN gene. Comparison can be made by (partial) sequencing, gel migration, hybridization, etc.

In another particular embodiment, the method comprises detecting all or part of an ICHTHYIN gene in the sample by selective hybridisation to a specific nucleic acid probe. Another method of the invention comprises the amplification of an ICHTHYIN gene or a portion thereof, and the determination of the presence of an alteration in the amplification product.

In particular embodiments, ICHTHYIN gene alterations are assessed by quantitative RT-PCR, LCR (Ligase Chain Reaction), TMA (Transcription Mediated Amplification), PCE (an enzyme amplified immunoassay) or bDNA (branched DNA signal amplification) assays.

In a particular embodiment, an ICHTHYIN gene alteration is determined by in vitro or ex vivo cDNA synthesis, (PCR) amplification with ICHTHYIN-specific oligonucleotide primers, and analysis of PCR products.

RT-PCR amplification of an ICHTHYIN mRNAs or gene may be performed using any pair of ICHTHYIN-specific primers. In particular any primers can be designed by the skilled artisan, such as any fragment of an ICHTHYIN gene, for use in the amplification step and especially a pair of primers comprising a forward sequence and a reverse sequence wherein said primers of said pair hybridize with a region of an ICHTHYIN gene (or flanking an ICHTHYIN gene) and allow amplification of at least a portion of the ICHTHYIN gene or of a portion of the ICHTHYIN gene containing a genetic alteration. In a particular embodiment, the ICHTHYIN cDNA can be prepared by using current protocol with a first primer set: RT4A 5' GCCACGCGGGG-GACAAT 3' (SEQ ID No 3) and AK1M 5' CCTGCAG-GCACTGATGTAAA 3' (SEQ ID No 4); and a second primer set selected from the group consisting of:

```
RT2A  5'  GACAAGTCGCGGCCACCT 3'        (SEQ ID No 5)
and

AK3M  5'  CTCAAGAAAAGAGAGCCCATTG 3';   (SEQ ID No 6)
```

```
-continued
RT3A  5'  ACAAGTCGCGGCCACCTG 3'        (SEQ ID No 7)
and

RT4M  5'  CAGGAAGTTCTGCCACCATTG 3';    (SEQ ID No 8)
and

RT2A  5'  GACAAGTCGCGGCCACCT 3'        (SEQ ID No 7)
and

AK1M  5'  CCTGCAGGCACTGATGTAAA 3'.     (SEQ ID No 6)
```

Primers of this invention more preferably contain less than about 50 nucleotides even more preferably less than 30 nucleotides, typically less than about 25 or 20 nucleotides. Also, preferred primers usually contain at least 5, preferably at least 8 nucleotides, to ensure specificity. The sequence of the primer can be prepared based on the sequence of an ICHTHYIN gene, to allow full complementarity therewith, preferably. Specific examples of primers of this invention are provided in Table 2.

Nucleic acid probes of this invention comprise (or specifically hybridise to) all or a distinctive part of the nucleic acid sequence of the ICHTHYIN gene, preferably at least a distinctive part thereof, i.e., a portion comprising at least one of the above-mentioned mutations. The probes may comprise between 8 and 1000 nucleotides, or even more (e.g., the entire sequence of the gene). The probes are most preferably single stranded. The probes may be labeled using any known technique such as radioactivity, fluorescence, enzymatic, chemical, etc. This labeling can use for example Phosphor 32, biotin (16-dUTP), digoxygenin (11-dUTP).

It should be understood that the present invention shall not be bound or limited by particular detection or labeling techniques, which can essentially be applied to the ICHTHYIN gene using ordinary skills.

The invention also relates to kits for implementing the above methods comprising at least a primer or a probe specific for an ICHTHYIN gene and, optionally, reagents for a nucleic acid amplification or hybridization reaction. The reagents may include antibodies, probes, primers, devices, supports, etc.

The invention also relates to a nucleic acid comprising a mutated ICHTHYIN gene sequence or a distinctive portion thereof.

As shown in the example, the invention now demonstrates a correlation between the presence of an alteration in an ICHTHYIN gene in a subject and the presence, development or predisposition to a skin disorder.

Methods of Screening Biologically Active Compounds

In a further aspect, the present invention also relates to the use of an ICHTHYIN gene or polypeptide as a target for screening biologically active agents, particularly compounds active on dry skin disorders and/or on the hepoxillin pathway.

A particular object of this invention lies in methods of selecting or identifying biologically active compounds, comprising contacting a candidate compound with an ICHTHYIN protein or a related protein and determining whether said compound binds to or modulate the activity of said protein. Binding may be determined by any technique known per se in the art, including ligand displacement, competition assays, direct binding using labeled compounds, immunoprecipitation, gel migration, etc. Modulation of the activity may be determined by assessing any conformational change, or by determining or measuring any secondary signal mediated by ICHTHYIN or said related protein. The method may be carried out using ICHTHYIN or related protein or a fragment of thereof (for instance the ligand-binding domain), which may be in isolated form, immobilized on a support, expressed in a lipid membrane or by an intact cell.

In a particular embodiment, the method comprises contacting a test compound with a recombinant host cell expressing an ICHTHYIN (or related) protein or a fragment thereof, typically a ligand-binding fragment thereof, and selecting the compounds that bind said protein or modulates its activity. Such recombinant cells, which also represent particular objects of the present invention, may be any cell comprising a genetic construct encoding an ICHTHYIN (or related) protein, said cell expressing said protein as a membrane protein. The recombinant cell may be a prokaryotic cell or a eukaryotic cell. Examples of prokaryotic cells include bacterial cells, particularly E. coli. Eukaryotic cells include yeast cells (e.g., saccharomyces, Kluyveromyces, etc), mammalian cells, plant cells, insect cells, etc. Particular examples of mammalian cells include primary or established cell cultures from various species, including rodents, canine, equine, bovine, ovine, human, etc, and from various tissue cell type (e.g., keratinocytes, fibroblasts, hepatocytes, muscle cells, nervous cells, kidney cells, ovary cells, etc).

The recombinant cells may be prepared by conventional recombinant techniques, e.g., by introduction into a selected cell type of a genetic construct encoding an ICHTHYIN (or related) protein, under conditions allowing expression of said protein as a membrane protein. The genetic construct may be any plasmid, cosmid, artificial chromosome, virus, phage, episome, etc, which may be prepared according to techniques known in the art. The construct typically comprises, upstream from the coding sequence, a promoter region that causes expression of ICHTHYIN in the selected cell. The construct may also include an origin of replication, or a marker gene, or a homologous region (allowing site-specific integration into the cell's genome), an integrase, etc. The construct may be introduced into the cells (or their ancestors) by techniques known per se in the art, such as electroporation, calcium-phosphate precipitation, conjugation, naked DNA transfer, transfection, infection, etc. Introduction may be performed in the presence of facilitating agents, such as liposomes, cationic lipids, polymers, etc. The recombinant cells may be selected and cultivated under conventional conditions. Cell surface expression of ICHTHYIN or related protein may be verified by any binding assay, for instance in the presence of an antibody or ligand.

In this regard, a particular object of this invention is a genetic or nucleic acid construct comprising a nucleic acid sequence encoding an ICHTHYIN protein, under the control of a promoter, preferably a heterologous promoter. The heterologous promoter may be any promoter that does not control ICHTHYIN expression in a naturally occurring cell. Examples of such promoters include viral promoters (e.g., CMV, LTR, TK, SV40, etc), cell promoters (PGK, HAS, etc), bacterial promoters (Trp, Lac, etc), yeast promoters, as well as any artificial or chimeric promoter sequence. The construct may be incorporated into a vector as described above.

A particular aspect of this invention resides in a method of selecting or identifying biologically active compounds, comprising contacting a candidate compound with a recombinant host cell expressing a receptor selected from ICHTHYIN, NIPA1, NIPA2, LOC152519, FLJ13955 and dJ462023.2, or a ligand-binding fragment or sub-unit thereof, and selecting the compounds that bind said protein or modulate its activity.

An other particular aspect of this invention resides in a method of selecting or identifying a compound that modulates the arachidonic acid metabolism, comprising contacting a candidate compound with a recombinant host cell expressing a receptor selected from ICHTHYIN, NIPA1, NIPA2, LOC152519, FLJ13955 and dJ462023.2, or a ligand-binding fragment or sub-unit thereof, and selecting the compounds that bind said protein or modulate its activity.

The ligand-binding domain of ICHTHYIN is located in the NH2-terminal region of the protein, between amino acid residues 1 and 60. Accordingly, in the above selection methods, it is preferred to use a protein or polypeptide comprising at least amino acid residues 1 to 60 of an ICHTHYIN protein.

Preferred compounds of this invention are selected for their ability to bind the above proteins and to behave as agonists of the corresponding ligands.

Other methods of this invention comprise contacting a candidate molecule with a gene encoding said proteins, and selecting the molecules that bind to said gene or modulate the expression of said proteins. Particular molecules are those, which stimulate expression of said genes, particularly those that stimulate the transcriptional promoters of said genes.

Within the context of this invention, various candidate compounds may be tested in parallel, using different assay formats (microtitration plate, etc). The compound may be contacted with the cells for a sufficient period of time to allow binding to occur, and the binding or activity may be assessed as disclosed above. The invention is particularly suited to screen agonists of the ICHTHYIN receptor, or activators thereof.

Antibodies

Another aspect of this invention relates to an antibody that binds an ICHTHYIN polypeptide or a related protein. The antibody may be a polyclonal or a monoclonal antibody. Furthermore, the term antibody also includes fragments and derivatives thereof, in particular fragments and derivatives of said monoclonal or polyclonal antibodies having substantially the same antigenic specificity. These include antibody fragments (e.g., Fab, Fab'2, CDRs, etc), humanized antibodies, poly-functional antibodies, Single Chain antibodies (ScFv), etc. These may be produced according to conventional methods, including immunization of an animal and collection of serum (polyclonal) or spleen cells (to produce hybridomas by fusion with appropriate cell lines).

To produce polyclonal antibodies from various species, the antigen is generally combined with an adjuvant (e.g., Freund's adjuvant) and administered to an animal, typically by sub-cutaneous injection. Repeated injections may be performed. Blood samples are collected and immunoglobulins or serum are separated. Monoclonal antibodies may be produced from various species as described for instance in Harlow et al (Antibodies: A laboratory Manual, CSH Press, 1988). Briefly, these methods comprise immunizing an animal with the antigen, followed by a recovery of spleen cells, which are then fused with immortalized cells, such as myeloma cells. The resulting hybridomas produce the monoclonal antibodies and can be selected by limit dilutions to isolate individual clones. Antibodies may also be produced by selection of combinatorial libraries of immunoglobulins, as disclosed for instance in Ward et al (Nature 341 (1989) 544).

Fab or F(ab')2 fragments may be produced by protease digestion, according to conventional techniques. Humanized antibodies can be prepared as previously described (Jones 1986; Riechmann 1988).

Preferred antibodies of this invention are prepared by immunization with a fragment of an ICHTHYIN polypeptide or related protein, preferably with an immunogenic fragment thereof, e.g., a fragment comprising at least an epitope, preferably of at least 5 amino acids. In a preferred embodiment, the fragment of ICHTHYIN is the C-17-K peptide (SEQ ID No 9): Cys Asp Asn Ile Glu Leu Ala Ser Thr Ser Ser Pro Glu Glu Lys Pro Lys.

Other preferred antibodies are monoclonal antibodies that specifically bind an altered ICHTHYIN polypeptide, particularly a mutated ICHTHYIN polypeptide.

The antibodies may be coupled to heterologous moieties, such as toxins, labels, drugs or other therapeutic agents, covalently or not, either directly or through the use of coupling agents or linkers.

The antibodies of this invention have various applications, including therapeutic, diagnostic, purification, detection, prophylactic, etc. In vitro, they can be used as screening agents or to purify the antigen from biological samples. They can also be used to detect or quantify the presence (or amounts) of an ICHTHYIN polypeptide in a sample collected from a subject, typically a blood sample from a mammalian, specifically a human subject. Antibodies of this invention may also be used as agonists or antagonists of the ICHTHYIN receptor, particularly in a therapeutic context.

Novel Compounds and Methods for Treating Skin Disorders

As mentioned above, the present invention discloses a novel metabolic pathway leading to hepoxilin with (R)-chirality, as well as its unexpected and undisclosed implication in skin disorders. The present application thus allows the design of novel therapeutic approaches to the treatment or prevention of particular skin conditions, using compounds from this metabolic pathway, as well as analogs or agonists thereof, or compounds that regulate the expression of genes involved in this metabolic pathway (see FIG. 5).

A particular object of this invention more specifically resides in the use of a compound selected from a metabolite of the 12(R)-hepoxilin pathway or an analog thereof (for instance, an ester derivative, an amide derivative), for the manufacture of a medication for the treatment of a skin disorder or a dry skin condition. The compound is preferably selected from the group consisting of 12(R)-TXA3, 12(R)-HXA3, 12(R)-HXA3-C, 12(R)-HXA3-D and 12(R)-HXA3-E (FIG. 3).

12-(R)-TXA-3 designates 12-(R)-Trioxilin A-3, i.e., 8,11R,12R-trihydroxyeicosa-(5Z,9E, 14Z)-trienoïc acid (formula $C_{20}H_{34}O_5$).

12-(R)-HXA-3 designates 12-(R)-Hepoxilin A-3, i.e., 8-(R,S)-hydroxy-(11R,12R) -epoxyeicosa-(5Z,9E,14Z)-trienoïc acid (formula $C_{20}H_{32}O_4$).

12-(R)-HXA-3-C designates 12-(R)-Hepoxilin A-3-C, i.e., 8-(R,S)-hydroxy-(11S) -glutathionyl-(12R)-hydroxyeicosa-(5Z,9E,14Z)-trienoïc acid (formula $C_{30}H_{49}N_3O_{10}S$).

12-(R)-HXA-3-D designates 12-(R)-Hepoxilin A-3-D, i.e., 8-(R,S)-hydroxy-(11S) -cysteïnylglycinyl-(12R)-hydroxyeicosa-(5Z,9E,14Z)-trienoïc acid (formula $C_{25}H_{42}N_2O_7S$).

12-(R)-HXA-3-E designates 12-(R)-Hepoxilin A-3-E, i.e., 8-(R,S)-hydroxy-(11S) -cysteïnyl-(12R)-hydroxyeicosa-(5Z,9E,14Z)-trienoïc acid (formula $C_{23}H_{39}NO_6S$).

Those compounds may be prepared in vitro from arachidonic acid using native or recombinant12R-lipoxygenase encoded by human ALOX12B gene, 12R-epoxide isomerase encoded by human ALOXE3 gene, an epoxide hydrolase (human soluble or ), or a glutathione S-transferase, a glutamyl transpeptidase, a dipeptidase, or combinations of those enzymes (FIG. 5). Synthetic methods for the preparation of racemic HXA3 have also been reported (39-40).

An analog of the metabolite may be any compound having the same type of biological activity. Typically, the analog is a synthetic molecule, having essentially the same core structure, which may contain additional or alternative substituting groups or chemical functions. Such analogs may be produced by drug design techniques, which are known in the art. Analogs include substituted or derivatized forms of the metabolite having an increased stability, in vivo half-life or which can be more easily produced. The term analog particularly encompasses a pro-medicament, i.e., a compound that is transformed in vivo into the metabolite. Such analogs may be screened using any one of the above disclosed screening methods.

In a more particular embodiment, the compound is a ligand of an ICHTHYIN protein, particularly identified or selected using a screening method as described above.

In a specific, preferred embodiment, the compound is 12(R)-TXA3 or an agonist thereof, i.e., a compound that binds the same receptor and causes activation thereof.

In this respect, a particular object of this invention resides in the use of 12(R)-TXA3 or an agonist or synthetic analog thereof, for the manufacture of a medication (or composition) for the treatment of a skin disorder, including dry skin (xerosis) and protection of skin in inflammatory disorders and other aggressions.

The present invention also relates to methods of treating a skin disorder, comprising administering to a subject in need thereof an amount of a metabolite of 12(R)-hepoxilin pathway or an analog thereof effective for treating said disease. The compounds may be administered through various routes, including oral, systemic and topical routes, particularly by topical administration. The compounds may be formulated in any appropriate buffer or excipient, such as saline solutions, isotonic buffer, gel, paste, ointment, etc.

In this respect, an other object of this invention is a composition, particularly a cosmetic composition, comprising a metabolite of 12(R)-hepoxilin pathway, or an analog thereof, and a pharmaceutically acceptable carrier, particularly for topical application.

A particular composition of this invention comprises 12(R)-TXA3 or an agonist or synthetic analog thereof, and a pharmaceutically acceptable carrier, particularly for topical application.

For topical administration, the composition may be in the form of an ointment, gel, cream, soap, foam, salve, spray and the like. Suitable excipients include any vehicle or agent that is non-toxic in vivo. For topical application to the skin, the composition may be in the form of an aqueous or oily solution, suspension or dispersion, which may be liquid or semi-liquid, such as a lotion, serum, milky preparation, etc. The composition may be in emulsified form, either oil-in-water or water-in-oil can. It may also be in the form of an anhydrous cream or gel, microparticles, dispersion, etc.

Suitable excipients may include solubilizing agents, stabilizing agents, penetrants, emulsifying agents, surfactants, etc., either alone or in combination(s). The cosmetic composition may also contain additional agents such as gelling agents, antioxidants, solvents, flavoring agents, preservatives, etc. The respective amounts of these agents may be adjusted by the skilled artisan, typically within the range of 0.01% to 15% of the total weight of the composition. Suitable emulsifiers for use in the present invention include, without limitation, glycerol, polysorbate and stearate. Suitable gelling agents include, without limitation, carboxyvinyl and acrylic copolymers, polysaccharides (e.g., hydroxypropylcellulose), polyacrylamides, clays, aluminium stearates, ethylcellulose and polyethylene. If appropriate, for topical administration, a thickening agent such as methyl cellulose may be used as well.

For oral administration, the compounds may be formulated into any conventional dosage form, including tablets, capsules, ampoules, etc. For transmucosal or transdermic administration, they may be formulated in the presence of penetrants, as gels, sprays, patch, etc.

The above methods, uses and compositions can be used to treat skin disorders, either alone or in combination with other agents, including to reduce the progression, prevent the development, suppress any symptoms or completely abolish the disease. The compounds may be administered according to various protocols, which may be adjusted by the practitioner, including the use of repeated administrations. Typical dosages may vary for instance from 0,01 to 1000 mg of active agent per dose.

As disclosed above, the skin disorder is selected from a group of dry skin disorders, particularly a dermatosis such as atopic skin, contact dermatitis, eczema, a psoriasis, or a keratinization disorder such as an ichthyosis and a palmoplantar keratoderma.

In another aspect, the skin disorder is selected from any skin inflammation or aggression, including burnt skin, acid, UV, etc.

The invention also relates, generally, to a pharmaceutical composition comprising an agonist or an antagonist of an ICHTHYIN protein (such as an antibody or a fragment thereof, or any synthetic molecule), in combination with a pharmaceutically acceptable vehicle or excipient, particularly for topical administration.

Further aspects and advantages of this invention will be disclosed in the following examples, which should be considered as illustrative and not limiting the scope of this application.

Mutations in ICHTHYIN. Sequences are shown in 2 affected patients from families F4 and F10, one parent, and one normal control.

Figure 2:
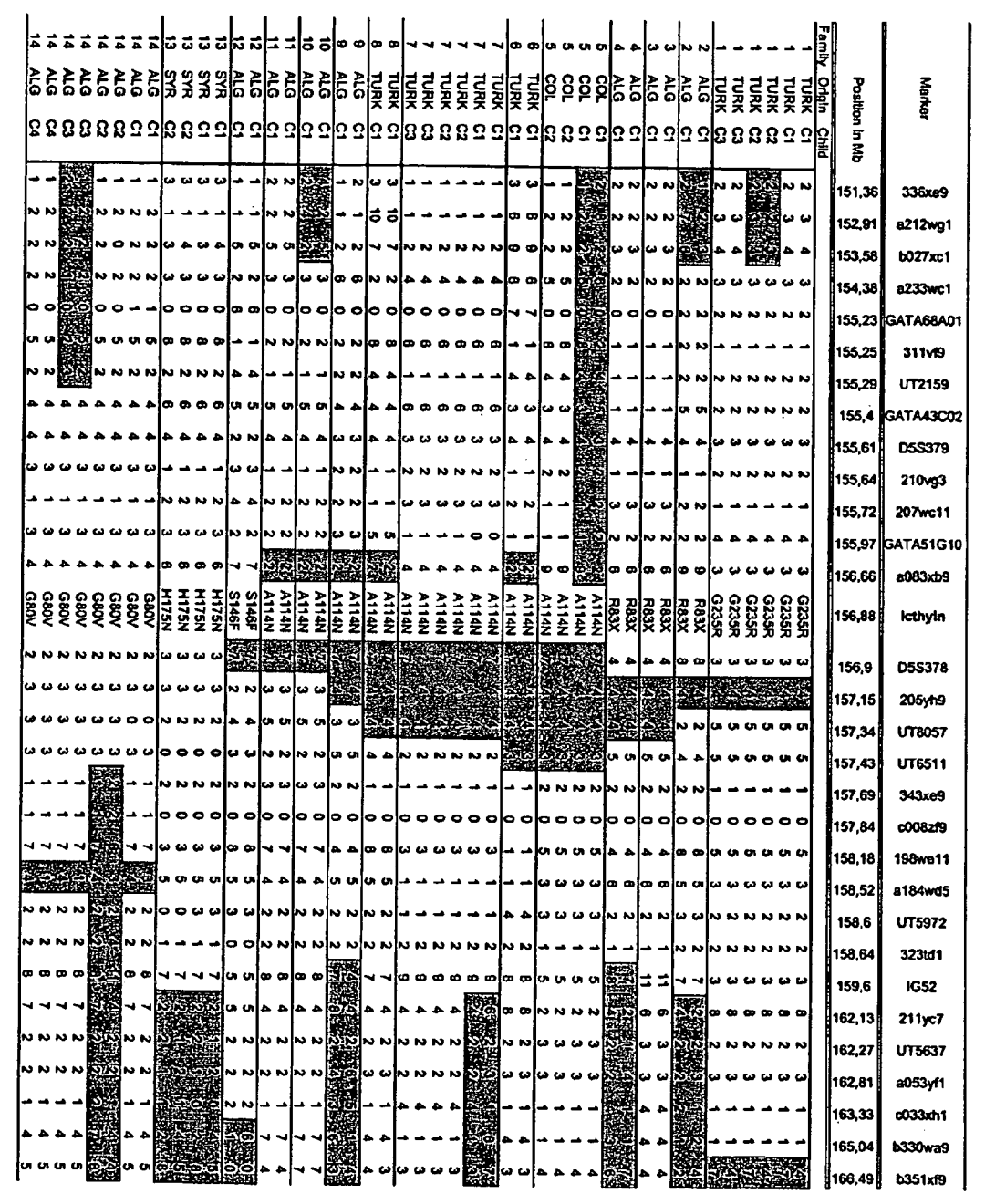

FIG. 2: Patient's haplotypes and corresponding mutations. Loss of homozygosity is indicated by gray color. Inside the smallest segregating interval between markers a083xb9 and D5S378, mutations and common alleles are in red. Allele number is indicated as 0 when no genotyping result is available. Paternal and maternal alleles for each affected child are presented.

FIGS. 3A and 3B: Structure of active compounds of this invention.

FIG. 4: Nucleotide sequence of an ICHTHYIN gene coding portion (SEQ ID NO:1).

Figure 5A:
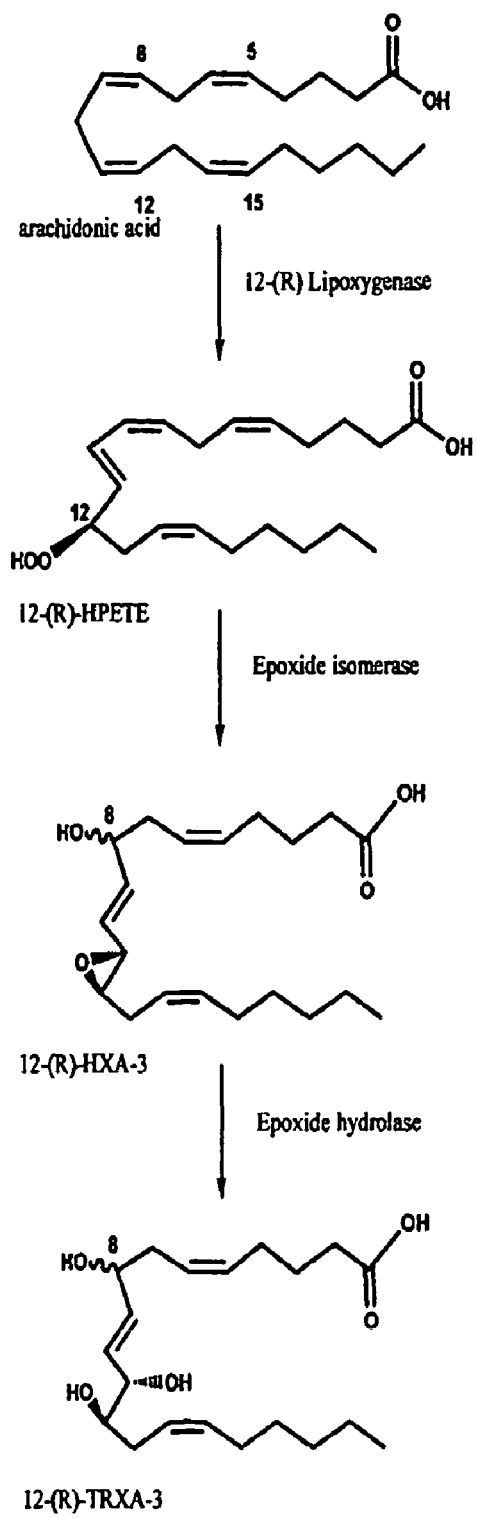
Figure 5B:
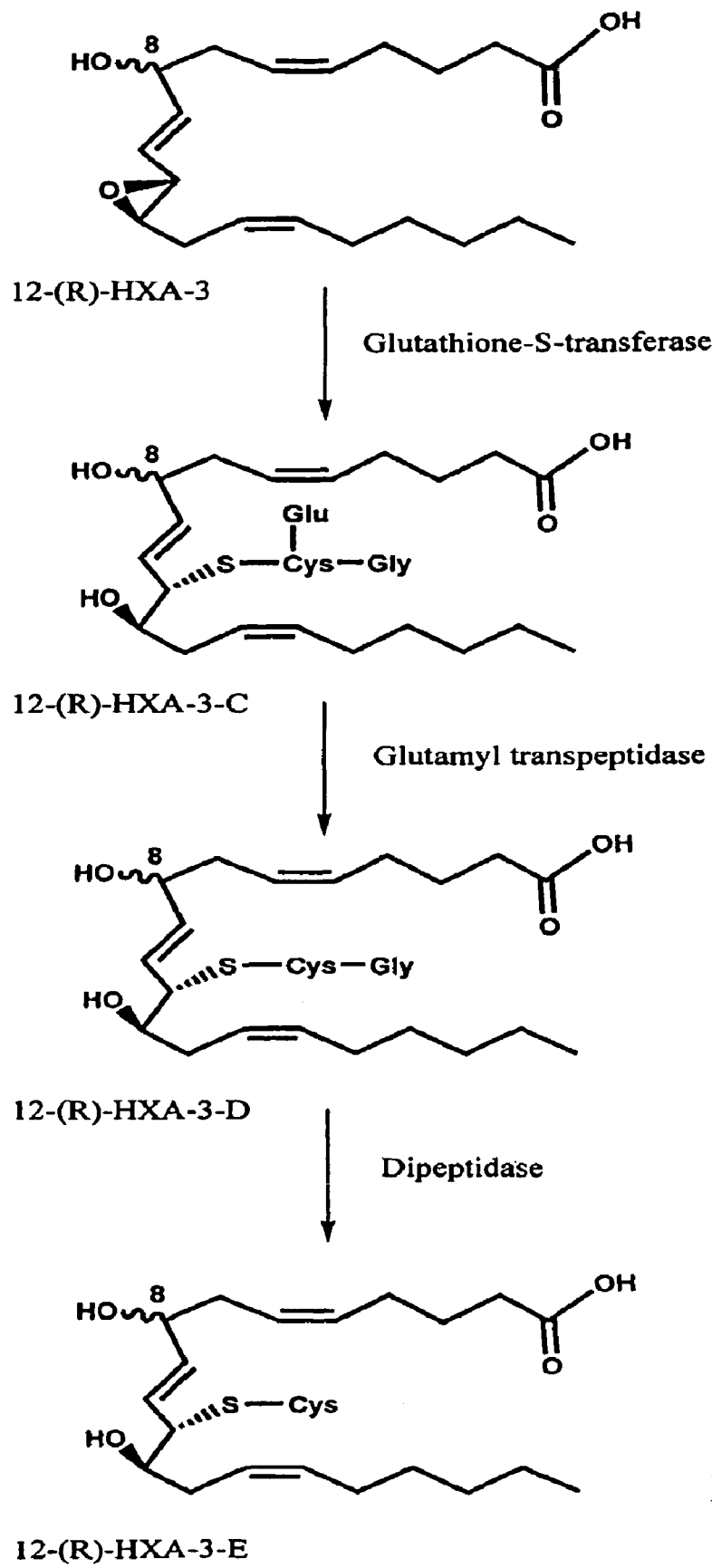

FIGS. 5A and 5B: A novel metabolic pathway

EXAMPLES

Materials and Methods

Subjects and Samples

The dermatologists recorded the clinical data and pedigree information of the families. Blood samples were collected from each participating family member after obtaining written informed consent. DNA extraction from peripheral blood leukocytes and establishment of cell lines were performed using standard procedures.

Genetic Analysis

Genotyping was carried out using 400 highly polymorphic microsatellite markers from the ABI panel (Linkage Mapping Set2, LMS2, Applied Biosystems) and a MegaBase capillary sequencer for the genome-wide scan. ABI 377 sequencers were used for fine mapping with publicly available microsatellites. Haplotypes were constructed assuming the most parsimonious linkage phase. Linkage programs were used based on the assumption of autosomal recessive inheritance, full penetrance and a disease frequency of 1/500,000 in the general population. Pairwise LOD scores were calculated with the MLINK program of the LINKAGE 5.1 package (36) incorporating consanguineous loops into the pedigree files.

Mutation Screening

Mutation analysis was performed in affected patients and in both parents in the 14 families, and in supplementary non-affected sibs in cases of missing parents. The inventors designed intronic oligonucleotide primers flanking the exons for amplification and sequencing the ICHTHYIN gene (Table 2) using the Primer3 program (http://www-genome.wi.mit-.edu/genome_software/other/primer3.html) (37). Sets of PCR conditions were used as indicated in Table 2. The touch-down PCR reaction was performed in a 45 µl volume containing 50 ng of genomic DNA (in 5 µl) with Hot Master™ Taq DNA polymerase (Eppendorf): initial denaturation step at 95° C. for 5 min, 6 cycles of amplification consisting of 40 s at 94° C., 30 s 68° C., and a 30 s elongation step at 72° C., followed by 30 cycles of 40 s at 94° C., 30 s at optimal annealing temperature, 30 s at 72° C., and a 5 min terminal elongation step. One to 2 µl of purified PCR products were added to 0.5 µl of sense or antisense primer (20 µM) and 2 µl of BigDye terminator mix (Applied Biosystems) in a 15 µl volume. The linear amplification consisted of an initial 5 min denaturation step at 96° C., 25 cycles of 10 s of denaturation at 96° C. and a 4 min annealing/extension step at 56-60° C. The reaction products were purified and sequenced on an Applied Biosystems Sequencer 3700. The forward or reverse strands from all patients and controls were sequenced for the entire coding region and the exon/intron boundaries. The sequences were analysed with the Phred Phrap program on Unix.

Lymphoblastoid, Keratinocyte and Fibroblast Cell Cultures, and RNA Extraction

Lymphoblastoid cell lines were established using standard procedures. Total RNA from lymphocytes was extracted with the RNA-PLUS (Quantum-Appligene) kit following the manufacturer's instructions. Human keratinocytes and fibroblasts were obtained from skin removed during routine plastic surgery of a normal individual. The skin sample was processed for primary keratinocyte culture and cells were grown according to the standard procedure described by Invitrogen Life Technologies using products from the same company in serum-free keratinocyte medium supplemented with bovine pituitary extract (25 µg/ml) and recombinant epidermal growth factor (0.1 ng/ml). For primary fibroblast culture the inventors used DMEM (Dulbecco's Modified Eagle's Medium) with 10% fetal calf serum and 2% L-glutamine. Cultures were grown for two passages and harvested when they reached 90% confluence. Total RNA was isolated using the QIAamp RNA Mini Protocol for isolation of total RNA from cultured cells (QIAGEN) following the manufacturer's instructions. The mRNA was isolated following the Oligotex direct mRNA protocol as provided by the manufacturer (QIAGEN).

5'-RACE (Rapid Amplification of cDNA Ends) and Cloning of the Amplification Products 5'-RACE was performed with Marathon-Ready cDNA from melanoma, placenta and stomach (Clontech) using Advantage 2 Polymerase Mix (Clontech) following the manufacturer's instructions. The PCR was run with AP1 primer and one of the five gene-specific antisense primer which the inventors designed from the cDNA sequence, starting with an initial denaturation step at 94° C. for 1 min, 30 cycles at 94° C. for 30 s and 68° C. for 4 min. To visualize the PCR products, they were loaded on a 2% agarose gel.

RT-PCR and Rapid-Scan™ Gene Expression Panel

RT-PCR was performed using the RT-PCR kit (Life Technologies) with oligo dT primers to generate the first strand of cDNA. Amplification of cDNA from keratinocytes, fibroblasts, placenta and lymphocytes was performed with four primer pairs (Table 2) covering the entire coding region, the 3'UTR and the 5'UTR region.

A gene expression panel including 24 human tissues was tested following the manufacturer's instructions (Rapid-Scan, OriGene Technologies) using primer pair RT_4 which is specific for the ICHTHYIN transcript. Expression in keratinocytes, fibroblasts, placenta and lymphocytes was also tested.

Additional Accession Numbers

Online Mendelian Inheritance in Man (http://www.ncbi.nlm.nih.gov/Omim): Abhydrolase domain containing 5 (ABHD5), previously CGI58, Comparative Gene Identification 58 [CGI58; MIM 604780]; Arachidonate lipoxygenase 3 [ALOXE3; MIM 607206]; Arachidonate 12-lipoxygenase, R type [ALOX12B; MIM 603741]; ATP-binding cassette, subfamily A, member 12 [ABCA12; MIM 607800]; Chanarin-Dorfman syndrome [CDS; MIM 275630]; Ichthyosis non-lamellar and nonerythrodermic congenital [NNCI; MIM 604781]; Lamellar ichthyosis [LI; MIM 242300]; Lamellar ichthyosis 1 [LI1; MIM 604777]; Lamellar ichthyosis 2 [LI2; MIM 601277]; Lamellar ichthyosis 3 [LI3; MIM 604777]; Lamellar ichthyosis 5 [LI5; MIM 606545]; Nonbullous ichthyosiform erythroderma [NCIE1, MIM 242100]; Nonbullous ichthyosiform erythroderma [NCIE2, MIM 604780]; Nonimprinted gene in Prader-Willi syndrome/Angelman syndrome chromosome region 1 [NIPAI; MIM 6008145]; Nonimprinted gene in Prader-Willi syndrome/Angelman syndrome chromosome region 2 [NIPA2; MIM 6008146]; Presenilin 1 [PSEN1; MIM 104311]; Transglutaminase 1 [TGM1; MIM 190195]; Spastic paraplegia 6, autosomal dominant [SPG6; MIM 600363].

Results

Clinical Features and Patient Origins

Figure 1:
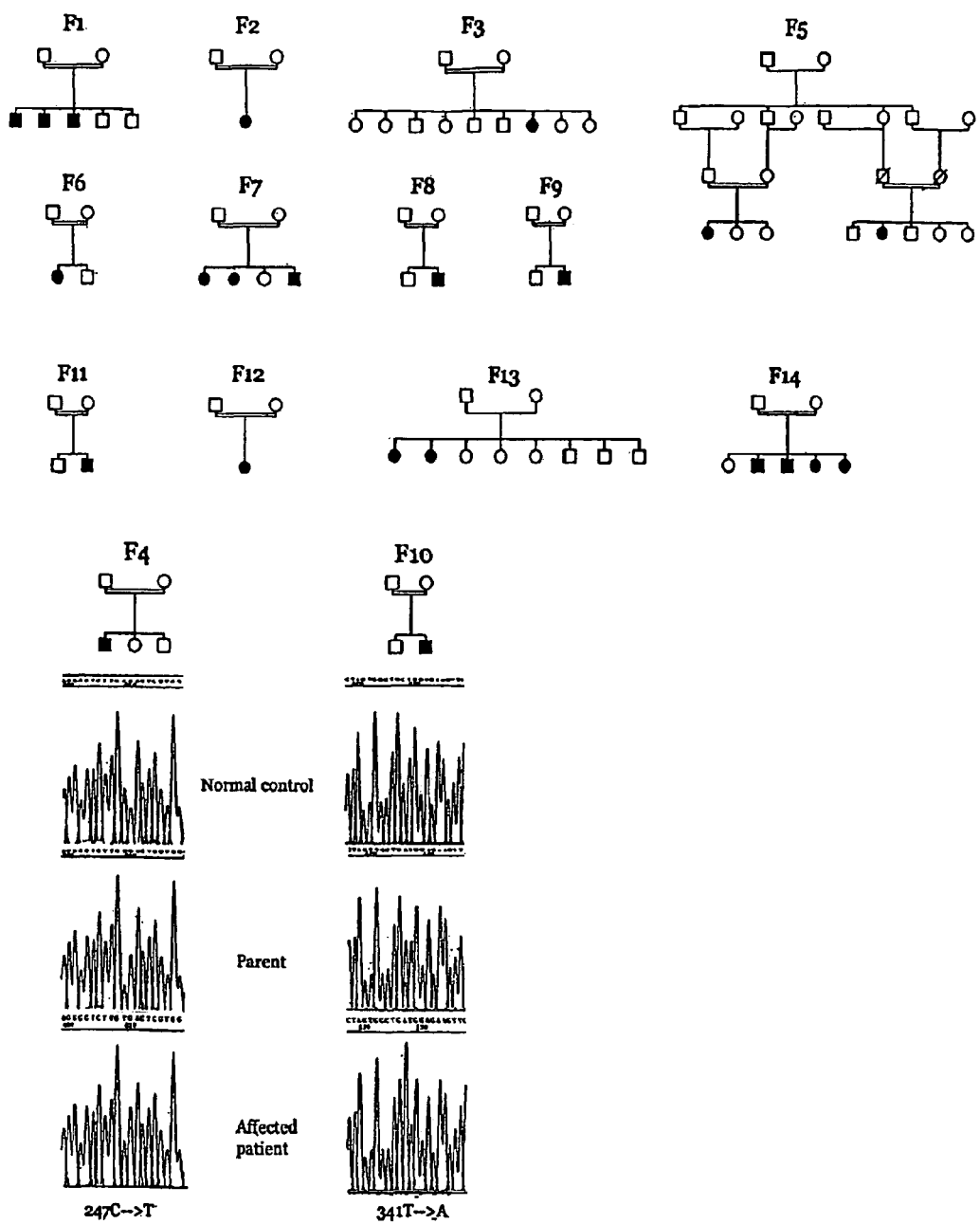
FIG. 1: Pedigrees of families F1 to F14.

The inventors analyzed 14 families comprising 23 patients (12 females, 11 males) and 50 non-affected family members. Individuals for whom DNA was available are shown in FIG. 1. All families are consanguineous from first cousin marriages, except two families in which the parents are 2nd cousins (F1) and 2nd cousins once removed (F14) (Table 1). Most families were from Mediterranean countries (eight from Algeria, four from Turkey, one from Syria), and one was from Colombia.

The majority of patients (60%) were born as collodion babies except for the patients from four Algerian families (F2, F4, F9, F14) and two Turkish families (F6, F8) who presented a clinical picture resembling NCIE. They presented generalized ichthyosis with erythema, fine whitish scaling on the face and trunk, and larger brownish scaling on the neck, buttocks and legs (see FIG. 2). However some of the families showed a more lamellar phenotype. All the patients presented palmoplantar keratoderma, often yellowish with fissures, and some had clubbing of nails.

Linkage, Linkage Disequilibrium and Haplotype Analysis

The inventors first localized the ICHTHYIN gene on chromosome 5q33.2-q34 by homozygosity mapping in two consanguineous families (F1 and F14) with three and four affected individuals. A region of homozygosity between the markers D5S410 (AFM191xd8) and D5S422 (AFM211yc7) was confirmed with a few additional microsatellite markers, before the inventors screened our DNA collection to find more families with ichthyosis linked to this new locus. A total of 81 families were analysed; 64 were consanguineous, and 17 were non-consanguineous but had more than one affected family member. The six known ichthyoses localizations were previously excluded in all of these families using our panel of 30 microsatellite markers covering the loci on chromosomes 2q33-35, 3p2, 14q11, 17p13, 19p12-q12, and 19p13.2-p13.1 (7-11). In 12 of these families (F2 to F13) linkage of ichthyosis to the new localization was found. The inventors then performed fine mapping with a total of 29 microsatellites (FIG. 2) in a 15.1 Mb interval between markers AFM336xe9 (D5S2077) and AFMb351xf9 (D5S2050). The maximum pairwise LOD score at Θ=0.00 for D5S378 was 16.38. A co-segregating region of 1 Mb was homozygous in all patients, defined by recombination events with loss of homozygosity in one patient from family 5 for the centromeric marker AFMa083xb9 (D5S2112), and in a patient from family 14 for the telomeric marker AFMb343xe9 (D5S2049). The results of genotyping are presented in FIG. 3. Patients from seven families (F5 to F11) shared a haplotype for 2 to 5 markers (2-7-4-4-3) inside the interval including the gene; these seven families, which had different geographical origins (Algeria, Colombia and Turkey), were later shown to carry the same missense mutation. Three other families from Algeria (F2 to F4) exhibited the same nonsense mutation, but only two of them shared the same haplotype.

Exclusion of Candidate Genes and Identification of Mutations in a Novel Gene ICHTHYIN Five genes were sequenced in the initial 2.3 Mb interval between the markers UT2159 and AFMb343xe9 (LOC91937, HAVCR1, HAVCR2, CRSP9, MGC26988) and all 7 known genes in the refined 1 Mb interval (CYFIP2, PRO133 ADAM19, SOX30, FLJ20546, FLJ38273 and ENTH). No mutations were found in the coding regions or exon-intron boundaries of these 12 genes. The inventors started therefore to analyze the human mRNAs and ESTs from GenBank between the markers AFMa083xb9 (D5S212) and AFMb343xe9 (D5S2049). One mRNA (AK026158, AF131815) was of particular interest because it was highly expressed in epidermal tissues, including skin and keratinocytes. Sequencing of the corresponding gene revealed 6 different mutations.

Structure of the ICHTHYIN Gene and its cDNA

A new predicted sequence (XM_371777) of 3077 bp was proposed corresponding to a cDNA (AK026158, FLJ22505) of 3094 bp (including the poly-A tail), which codes for a protein of 404 amino acids. BLAST analysis between this mRNA and the BAC sequence AC008676 supported the existence of six exons as described in other public databases. The inventors performed 5'RACE with 5 different primers and subcloned some of these 5'RACE products, but the inventors failed to identify any elongation of the 5' end. The sequence was checked by overlapping RT-PCR, and the products were sequenced and compared with the sequences from public databases. BLAST analysis revealed one mouse (NM_172524) and one rat mRNA ortholog (XM_220330) showing homologies of 83% and 84% for the nucleotide sequence, and of 74% and 75% for the protein sequence respectively. The mouse mRNA of 3299 bp is reported to be full-length whereas the rat mRNA is only 1272 bp long. Multiple nucleotide alignments (http://prodes.toulouse.inra.fr/multalin/) of orthologs from human, mouse and rat showed a highly conserved sequence with a homology of 92%.

Mutation Analysis of the ICHTHYIN Gene

Sequencing of the six exons and of the exon-intron boundaries of the ICHTHYIN gene revealed six different homozygous mutations in the 14 consanguineous families (Table 1): one was a nonsense mutation and five were missense mutations: 247C→T (R83X) and 239G→T (G80V) in exon 2; 341C→A (A114D) in exon 4, 437C→T (S146F) and 523C→G (H175N) in exon 5; and 703G→A (G235R) in exon 6. The mutations were all situated in parts of the gene that are highly conserved between mice, rats and humans. None of these sequence variations were found in 100 normal chromosomes from a Mediterranean control population.

Expression Analysis

The inventors analyzed tissue expression by ICHTHYIN-specific RT-PCR with primer pairs RT_4 (Table 2) for a 1111 bp fragment using the RAPID-SCAN™ gene expression panel and RNAs from cultured keratinocytes, fibroblasts, placenta and lymphocytes (data not shown). The ICHTHYIN transcript was found to be expressed in most tissues tested; it was highly expressed in brain, lung, stomach, skin and leucocytes, and was present at a lower level in the other tissues, with the exception of liver, thyroid and fetal brain in which no expression was detectable. Strong expression of ICHTHYIN transcripts was observed in cultured keratinocytes from normal skin biopsies; expression was weaker in cultured fibroblasts from the same skin biopsies, in placenta and in lymphocytes.

Sequence Analysis of the ICHTHYIN Protein and Identification of Conserved Residues The sequence of 404 amino acids corresponds to a protein with a calculated molecular weight of 44 kDa. This sequence was submitted to the topology prediction programs for sequence signals, transmembrane (TM) domains and protein orientation available through the ExPASy server (www.expasy.org), to protein analyzing tools from the Biology WorkBench (http://biowb.sdsc.edu/) and to homology searches through protein databases (http://www.ncbi.nlm.nih.gov). The protein is predicted to localize in the plasma membrane, but does not possess a signal sequence. The protein was determined to contain 7-9 TM domains, using the PSORTII, SMART and BPROMPT programs and the Dense Alignment Surface (DAS) method. This structure defines a new family of proteins (PFAM: DUF803). Analysis using the ProtFun2.1 server (http://www.cbs.dtu.dk/services/ProtFun/) classifies ICHTHYIN in finctional and gene ontology categories under transport and binding activities.

A New Family of Proteins with Several TM Domains

BLAST analysis identified five human paralogs of ICHTHYIN (listed above), of which the first three are the most closely related to ICHTHYIN, with up to 57% of homology. Four of these genes have the same basic structure and between 5 and 8 exons: 1) NIPA1 (Non-Imprinted in Prader-Willi/Angelman syndrome 1) or SPG6 on chromosome 15q11.2; 2) NIPA2 (DUF803.0) also on chromosome 15q11.2; 3) LOC152519 (DUF803.3) on chromosome 4p12; 4) FLJ13955 (DUF803.1) on chromosome 8q22.2; and 5)dJ462023.2 (DUF803.4) on chromosome 1p36.12-p35.1.

The FLJ13955 and dJ462023.2 genes are predicted to have 12 exons, share high homology, around 50% with each other, and 25% with the other paralogs. Some of these sequences were annotated by automatic analysis pipelines such as GeneWise, Genscan, Gnomon, and could be either too long or incomplete, with the exception of NIPA1 and 2, which have been more completely analyzed (19, 20a). Two transcripts were found for NIPA1, one of 2.2 kb and a larger one of 7.5 kb with a long 3'UTR which is present at low levels in most tissues, but at higher levels in neuronal tissues (19).

Fifty-two homologues were found in eukaryotes including *Caenorhabditis elegans, Drosophila*, mice and plants (IPR008521; http://ebi.ac.uk/interpro/). Weaker BLASTP homologies were also found with a hypothetical transport protein in *Pseudomonas denitrificans* (ORF6; SW:YCB6_PSEDE) (20b), and with a *C. elegans* chemoreceptor with 7 TM domains of the sri family (WP:CE33629).

Multiple amino acid alignment confirms both the high homology and the conservation of the positions of the TM regions of the six proteins of the family (FIG. 3).

The phylogenetic tree (Tree Top, http://www.genebee.msu.su/services/phtree_reduced.html) of the multiple sequence alignments (CLUSTALW) of the six human DUF803 proteins and 347 human GPCR protein sequences from the GPCR database (GPCRDB, May 2003 release; http://www.gpcr.org/7tm/) identified DUF803 proteins as a branch between glutamate and frizzled/taste2 receptors (21).

The mutations identified in ICHTHYIN include a nonsense mutation in the second exon which would lead to the synthesis of a truncated protein. Four of the 5 missense mutations were situated inside one of the predicted TM domains, in the $2^{nd}$ (AA80), the $3^{rd}$ (AA146), the $4^{th}$ (AA175),- and the $6^{th}$ (AA235). The fifth mutation (AA114) is located between the $2_{nd}$ and $3^{rd}$ TM domains.

Genotyping on Chromosomes 15q11.2 and 8q22.2 and Mutation Analysis of NIPA2 and FLJ13955 in Families in which other Known loci had been Excluded.

Two of the ICHTHYIN paralogs, NIPA2 and FLJ13955, have been described to be strongly expressed in keratinocytes (SAGE). In order to test linkage, the localizations containing these paralogs in a form of ARCI, were genotyped in 65 consanguineous families (226 individuals including 103 affected family members): the 52 remaining consanguineous families from our DNA collection and 13 new consanguineous families. Linkage to chromosome 8q22.2 or 15q 11.2 was suggested in twelve families but when the two candidate genes were sequenced for the exons and exon/intron boundaries, no mutations were found.

Method for Screening Agonists and Antagonists
  1) Cloning of double stranded cDNA: The cloning of ichthyin's doubled stranded cDNA has been performed using standard methods and kits (SuperScript Double-Stranded cDNA Synthesis kit). The ichthyin specific primers for this doubled stranded cDNA are indicated in the detailed description.

2) Expression studies in viral vectors: The complete double stranded cDNA will then be expressed in several vectors after standard methods for
   a. The establishment of permanent cell lines,
   b. The co-transfection experiments with a reporter GPCR gene,
   c. The analysis of ions (Ca, Cl, H) fluxes,
   d. The analysis of the expression of the other genes implicated in ARCI.
3) Chemical synthesis of (R)-trioxilin A3:
   a. The metabolites such as (R)-trioxilin A3 will be chemical synthetized.
   b. They will be labeled with isotopes in order to performed binding experiments.
   c. The biological activity of trioxilin as a key regulator with induction of experssion of the other genes implicated in ARCI (Quantitative PCR of RNA from the cells of patients with mutations in TGM1, ABCA12, ALOX12B, ALOXE3, ABHD5, Ichthyin, STS, ALDH3A2) will be studied.

4) the screening of agonists and antagonists in the binding experiments will be performed.

TABLE 1

Origin of families and mutations

| Family | Number of patients | Consanguinity Degree | Origin | Mutation | Effect | Exon |
|---|---|---|---|---|---|---|
| 1 | 3 | $1^{st}$ | Turkey | 703G→A | G235R | 6 |
| 2 | 1 | $1^{st}$ | Algeria | 247C→T | R83X | 2 |
| 3 | 1 | $1^{st}$ | Algeria | 247C→T | R83X | 2 |
| 4 | 1 | $1^{st}$ | Algeria | 247C→T | R83X | 2 |
| 5 | 2 | $1^{st}$ | Colombia | 341C→A | A114D | 4 |
| 6 | 1 | $1^{st}$ | Turkey | 341C→A | A114D | 4 |
| 7 | 3 | $2^{nd}$ | Turkey | 341C→A | A114D | 4 |
| 8 | 1 | $1^{st}$ | Turkey | 341C→A | A114D | 4 |
| 9 | 1 | $1^{st}$ | Algeria | 341C→A | A114D | 4 |
| 10 | 1 | $1^{st}$ | Algeria | 341C→A | A114D | 4 |
| 11 | 1 | $1^{st}$ | Algeria | 341C→A | A114D | 4 |
| 12 | 1 | $1^{st}$ | Algeria | 437C→T | S146F | 5 |
| 13 | 2 | $1^{st}$ | Syria | 523C→G | H175N | 5 |
| 14 | 4 | $2^{nd}$ | Algeria | 239G→T | G80V | 2 |

TABLE 2

Primer sequences for ICHTHYIN and paralogs: exon amplification and RT-PCR

| Name | Forward sequences | Reverse sequences | PCR-conditions | Length (bp) of amplicon |
|---|---|---|---|---|
| Exon amplification | | LOC348938 | | |
| 1 | ctcacctcttgccc ctagc SEQ ID No 10 | gccagaacccaga tcttcaa SEQ ID No 11 | IX | 520 |
| 2 | ttatctggcacgtg gtggta SEQ ID No 12 | aggtgggattcca gataggg SEQ ID No 13 | I | 595 |
| 3 | gcctgtgaggaatc caagag SEQ ID No 14 | ctgggcctcagat tcacact SEQ ID No 15 | I | 442 |
| 4 | ctccagggagagag cgtatg SEQ ID No 16 | ggcctgcctctct attaccc SEQ ID No 17 | I | 452 |
| 5 | gaacaatgtctccc gtggat SEQ ID No 18 | ccatacatatcag gccaggaa SEQ ID No 19 | I | 599 |
| 6 | ttgggggtttaaaa acctaacc SEQ ID No 20 | cagttgcactgga aaataacca SEQ ID No 21 | II | 898 |
| RT-PCR | | | | |
| RT_4 | gggcaaaggaatat cctcatct SEQ ID No 22 | aagaggaagtgac aaaggcaac SEQ ID No 23 | VII | 1111 |
| RT_7 | ccacgcgggggaca agtcgc SEQ ID No 24 | gcaggtgcaaatg cgtaggctccaaa g SEQ ID No 25 | VII | 474 |
| RT_8 | cgtcggcgtgtgcc ccgg SEQ ID No 26 | gcaggtgcaaatg cgtaggctccaaa g SEQ ID No 27 | VII | 409 |
| RT_10 | ctttggagcctacg catttgcac SEQ ID No 28 | ggacgaggtaacg accaccgtgg SEQ ID No 29 | VII | 574 |

TABLE 2-continued

Primer sequences for ICHTHYIN and paralogs: exon amplification and RT-PCR

| Name | Forward sequences | Reverse sequences | PCR-conditions | Length (bp) of amplicon |
|---|---|---|---|---|
| Exon amplification paralogs FLJ13955 | | | | |
| 1 | caggctgggagcac ctac SEQ ID No 30 | gggtgtcttcctg agagctg SEQ ID No 31 | VIII | 418 |
| 2 | ccaaacctaccctg ggaaat SEQ ID No 32 | atgcactccagcc tgaatta SEQ ID No 33 | VI | 378 |
| 3 | gcattcccctcata gctcag SEQ ID No 34 | catgacaatggat cgctgaa SEQ ID No 35 | I | 394 |
| 4 | ccacatatcctcag ccacag SEQ ID No 36 | agatggcagctcc aagacag SEQ ID No 37 | I | 400 |
| 5 | aatgtggacgctat ccaagg SEQ ID No 38 | gggtgcttctgtt gctgact SEQ ID No 39 | I | 455 |
| 6 | acgttcgagctctg ggtct SEQ ID No 40 | aaccatgagaaag gagtagaatgc SEQ ID No 41 | I | 379 |
| 7 | gcaacaaggccact gcttac SEQ ID No 42 | ggctgaggacaag ctacagg SEQ ID No 43 | I | 447 |
| 8 | tgactgctgattgg aaatgc SEQ ID No 44 | aacctctcctgga agattgtca SEQ ID No 45 | VI | 389 |
| 9 | agaatgtgtggcat gcaaat SEQ ID No 46 | aggagctcaggaa actgatgtt SEQ ID No 47 | I | 360 |
| 10 | ccatgagaaactgg aagaacaa SEQ ID No 48 | cactgaaaatagc acctttggtt SEQ ID No 49 | II | 371 |
| 11 | ctgcaccgagcctg attatt SEQ ID No 50 | tgaaacgccatgt ctgtagc SEQ ID No 51 | I | 300 |
| 12 | cttctctttagaga gtgcccaca SEQ ID No 52 | gtggggaaagga ctgaaat SEQ ID No 53 | II | 374 |
| NIPA2 | | | | |
| 1 | actggggccttgta aaggaa SEQ ID No 54 | aggaaaaccgctt cagaaca SEQ ID No 55 | V | 507 |
| 1_alternative | agtaagctgcctgt cgaagc SEQ ID No 56 | caagaccttggct cagaaaaa SEQ ID No 57 | I | 458 |
| 2 | tgaagaaatataca ggttggtgct SEQ ID No 58 | cacgaggaatgaa gatgtgg SEQ ID No 59 | II | 491 |
| 3 | agaaatcccgagtc atgcag SEQ ID No 60 | agcctgggtgaca gagtgag SEQ ID No 61 | IV | 346 |
| 4 | ctgggcgacagagt gagact SEQ ID No 62 | aagcgaagttctc caggttg SEQ ID No 63 | III | 385 |

TABLE 2-continued

Primer sequences for ICHTHYIN and paralogs: exon amplification and RT-PCR

| Name | Forward sequences | Reverse sequences | PCR-conditions | Length (bp) of amplicon |
|---|---|---|---|---|
| 5 | gcgaaagccagaat cttcat SEQ ID No 64 | caggcttgggatt gatagga SEQ ID No 65 | II | 454 |
| 6_1 | gcttgggctgcaaa ataaag SEQ ID No 66 | gacgtctttaaag gcatgcaa SEQ ID No 67 | II | 599 |
| 6_2 | gagcctcatcgtct gtgtga SEQ ID No 68 | cgtcatgtgctga ggtcatt SEQ ID No 69 | II | 618 |
| RT-PCR paralogues | | FLJ13955 | | |
| RT3 | cttcagctggcaca acaaga SEQ ID No 70 | tggcaccactgtt gtcgtat SEQ ID No 71 | VII | 624 |
| RT4 | tgattctgctaacc ctggtg SEQ ID No 72 | ataacaggccaac agccatc SEQ ID No 73 NIPA2 | VII | 586 |
| RT3 | caaggtggccatgc atatct SEQ ID No 74 | gcaacaagaatat ccccacaa SEQ ID No 75 | VII | 748 |
| RT4 | gagcctcatcgtct gtgtga SEQ ID No 76 | cgtcatgtgctga ggtcatt SEQ ID No 77 NIPA1 | VII | 618 |
| RT1 | ggcccaagacatct tgcata SEQ ID No 78 | gctatccaccaga ccacctg SEQ ID No 79 LOC152519 | VII | 492 |
| RT1 | gggaccctgagtgg attctt SEQ ID No 80 | ccacctggcagag acaaag SEQ ID No 81 DJ462023.2 | VII | 517 |
| RT1 | ggaagaagcccatt ccattt SEQ ID No 82 | caggcagaggctg gattcta SEQ ID No 83 | VII | 493 |

PCR conditions:
I: As described in Material and Methods;
II: TM 55° C.;
III: TM 59° C. using Hot Master Taq (Eppendorf);
IV: TM 59° C., 100 ng of DNA;
V: TM 55° C. using Advantage GC genomic Polymerase Mix (Clontech);
VI: TM 55° C., 100 ng of DNA;
VII: RT-PCR As described in Material and Methods;
VIII: TM 60° C. using Advantage GC genomic Polymerase Mix (Clontech);
IX: TM 55° C. using Advantage GC genomic Polymerase Mix (Clontech), 100 ng of DNA.

REFERENCES

1. Williams, M. L. and Elias, P. M. (1985) Heterogeneity in autosomal recessive ichthyosis. Clinical and biochemical differentiation of lamellar ichthyosis and nonbullous congenital ichthyosiform erythroderma. *Arch. Dermatol.*, 121, 477-488.

2. Traupe, H. (1989) *The ichthyoses: a guide to clinical diagnosis, genetic counseling, and therapy.* Springer, Heidelberg, Germany.

3. Griffiths, W. A. D., Judge, M. R. and Leigh, I. M. (1998) *Disorders of keratinization.* In: Champion, R. H., Burton, J. L., Burns, D. A. and Breathnach, S. M. (eds) Rook/Wilkinson/Ebling: Textbook of Dematology. Blackwell Science, Oxford, pp 1483-1530.

4. Lavrijsen, A. P., Bouwstra, J. A., Gooris, G. S., Weerheim, A., Bodde, H. E. and Ponec, M. (1995) Reduced skin barrier function parallels abnormal stratum corneum lipid organization in patients with lamellar ichthyosis. *J. Invest. Dermatol.*, 105, 619-624.

5. Melnick, B. (1989) Epidermal lipids and the biochemistry of keratinization. In: Traupe, H. (ed) *The ichthyoses: a* guide to clinical diagnosis, genetic counseling, and therapy. Springer, Heidelberg, Germany, pp 14-42.
6. Hazell, M. and Marks, R. (1985) Clinical, histologic, and cell kinetic discriminants between lamellar ichthyosis and nonbullous congenital ichthyosiform erythroderma. *Arch. Dermatol.*, 121, 489-493.
7. Russell, L. J., DiGiovanna, J. J., Hashem, N., Compton, J. G. and Bale, S. J. (1994) Linkage of autosomal recessive lamellar ichthyosis to chromosome 14q. *Am. J. Hum. Genet.*, 55, 1146-1152.
8. Parmentier, L., Lakhdar, H., Blanchet-Bardon, C., Marchand, S., Dubertret, L. and Weissenbach, J. (1996) Mapping of a second locus for lamellar ichthyosis to chromosome 2q33-35. *Hum. Mol. Genet.*, 5, 555-559. Erratum in: (1996) *Hum. Mol. Genet.*, 5, 862-863.
9. Fischer, J., Faure, A., Bouadjar, B., Blanchet-Bardon, C., Karaduman, A., Thomas, I., Emre, S., Cure, S., Özgüc, M., Weissenbach, J. et al. (2000) Two new loci for autosomal recessive ichthyosis on chromosomes 3p21 and 19p12-q12 and evidence for further genetic heterogeneity. *Am. J. Hum. Genet.*, 66, 904-913.
10. Krebsova, A., Kuster, W., Lestringant, G. G., Schulze, B., Hinz, B., Frossard, P. M., Reis, A. and Hennies, H. C. (2001) Identification, by homozygosity mapping, of a novel locus for autosomal recessive congenital ichthyosis on chromosome 17p, and evidence for further genetic heterogeneity. *Am. J. Hum. Genet.*, 69, 216-222.
11. Virolainen, E., Wessman, M., Hovatta, I., Niemi, K. M., Ignatius, J., Kere, J., Peltonen, L. and Palotie, A. (2000) Assignment of a novel locus for autosomal recessive congenital ichthyosis to chromosome 19p13.1-p13.2. *Am. J. Hum. Genet.*, 66, 1132-1137.
12. Huber, M., Rettler, I., Bemasconi, K., Frenk, E., Lavrijsen, S. P., Ponec, M., Bon, A., Lautenschlager, S., Schorderet, D. F. and Hohl, D. (1995) Mutations of keratinocyte transglutaminase in lamellar ichthyosis. *Science*, 267, 525-528.
13. Russell, L. J., DiGiovanna, J. J., Rogers, G. R., Steinert, P. M., Hashem, N., Compton, J. G. and Bale, S. J. (1995) Mutations in the gene for transglutaminase 1 in autosomal recessive lamellar ichthyosis. *Nat. Genet.*, 9, 279-283.
14. Jobard, F., Lefèvre, C., Karaduman, A., Blanchet-Bardon, C., Emre, S., Weissenbach, J., Özgüc, M., Lathrop, M., Prud'homme, J. F. and Fischer, J. (2002) Lipoxygenase-3 (ALOXE3) and 12(R)-lipoxygenase (ALOX12B) are mutated in non-bullous congenital ichthyosiform erythroderma (NCIE) linked to chromosome 17p13.1. *Hum. Mol. Genet.*, 11, 107-113.
15. Lefevre, C., Audebert, S., Jobard, F., Bouadjar, B., Lakhdar, H., Boughdene-Stambouli, O., Blanchet-Bardon, C., Heilig, R., Foglio, M. et al. (2003) Mutations in the transporter ABCA12 are associated with lamellar ichthyosis type 2. *Hum. Mol. Genet.*, 12, 2369-2378.
16. Lefevre, C., Jobard, F., Caux, F., Bouadjar, B., Karaduman, A., Heilig, R., Lakhdar, H., Wollenberg, A., Verret, J. L., et al. (2001) Mutations in CGI-58, the gene encoding a new protein of the esterase/lipase/thioesterase subfamily, in Chanarin-Dorfinan syndrome. Am. J. Hum. Genet., 69, 1002-1012.
17. Cserzo, M., Wallin, E., Simon, I., von Heijne, G. and Elofsson, A. (1997) Prediction of transmembrane alpha-helices in procariotic membrane proteins: the Dense Alignment Surface method. *Prot. Eng.*, 10, 673-676.
18. Hirokawa, T., Boon-Chieng, S. and Mitaku, S. (1998) SOSUI: classification and secondary structure prediction system for membrane proteins. *Bioinformatics*, 14, 378-379.
19. Chai, J. H., Locke, D. P., Greally, J. M., Knoll, J. H., Ohta, T., Dunai, J., Yavor, A., Eichler, E. E. and Nicholls, R. D. (2003) Identification of four highly conserved genes between breakpoint hotspots BP1 and BP2 of the Prader-Willi/Angelman syndromes deletion region that have undergone evolutionary transposition mediated by flanking duplicons. *Am. J. Hum. Genet.*, 73, 898-925.
20. a) Rainier, S., Chai, J. H., Tokarz, D., Nicholls, R. D. and Fink, J. K. (2003) NIPA1 gene mutations cause autosomal dominant hereditary spastic paraplegia (SPG6). *Am. J. Hum. Genet.*, 73, 967-971. 20 b) Crouzet J, Levy-Schil S, Cameron B, Cauchois L, Rigault S, Rouyez M C, Blanche F, Debussche L, Thibaut D. (1991) Nucleotide sequence and genetic analysis of a 13.1-kilobase-pair Pseudomonas denitrificans DNA fragment containing five cob genes and identification of structural genes encoding Cob(I)alamin adenosyltransferase, cobyric acid synthase, and bifunctional cobinamide kinase-cobinamide phosphate guanylyl-transferase. *J. Bacteriol.*, 173, 6074-6087.
21. Fredriksson, R., Lagerstrom, M. C., Lundin, L. G. and Schioth, H. B. (2003) The G-protein-coupled receptors in the human genome form five main families. Phylogenetic analysis, paralogon groups, and fingerprints. *Mol. Pharmacol.*, 63, 1256-1272.
22. Bergers, M., Traupe, H., Dunnwald, S. C., Mier, P. D., van Dooren-Greebe, R., Steijlen, P. and Happle, R. (1990) Enzymatic distinction between two subgroups of autosomal recessive lamellar ichthyosis. *J. Invest. Dermatol.*, 94, 407-412.
23. Ghadially, R., Williams, M. L., Hou, S. Y. and Elias, P. M. (1992) Membrane structural abnormalities in the stratum corneum of the autosomal recessive ichthyoses. *J. Invest. Dermatol.*, 99, 755-763.
24. Yu, Z., Schneider, C., Boeglin, W. E., Mamett, L. J. and Brash, A. R. (2003) The lipoxygenase gene ALOXE3 implicated in skin differentiation encodes a hydroperoxide isomerase. *Proc. Natl. Acad. Sci. USA*, 100, 9162-9167.
25. Pace-Asciak, C. R. (1994) Hepoxilins: a review on their cellular actions. *Biochim. Biophys. Acta.*, 1215, 1-8.
26. Pace-Asciak, C. R., Reynaud, D., Demin, P. and Nigam, S. (1999) The hepoxilins. A review. *Adv. Exp. Med. Biol.*, 447, 123-132.
27. None
28. Chen, C. P., Kemytsky, A. and Rost, B. (2002) Transmembrane helix predictions revisited. *Protein Sci.*, 11, 2774-2791.
29. Lao, D. M., Okuno, T. and Shimizu, T. (2002) Evaluating transmembrane topology prediction methods for the effect of signal peptide in topology prediction. *In Silico Biol.*, 2, 485-494.
30. Wallin, E and von Heijne, G. (1995) Properties of N-terminal tails in G-protein coupled receptors: a statistical study. *Prot. Eng.*, 8, 693-698.
31. Kim, J. and Schekman, R. (2004) The ins and outs of presenilin 1 membrane topology. *Proc. Natl. Acad. Sci. USA*, 101, 905-906.
32. Qiao, N., Reynaud, D., Demin, P., Halushka, P. V. and Pace-Asciak, C. R. (2003) The thromboxane receptor antagonist PBT-3, a hepoxilin stable. analog, selectively antagonizes the TPalpha isoform in transfected COS-7 cells. *J. Pharmacol. Exp. Ther.*, 307, 1142-1147.
33. Brink, C., Dahlen, S. E., Drazen, J., Evans, J. F., Hay, D. W., Nicosia, S., Serhan, C. N., Shimizu, T. and Yokomizo, T. (2003) International Union of Pharmacology XXXVII. Nomenclature for leukotriene and lipoxin receptors. *Pharmacol. Rev.*, 55, 195-227.

34. Funk, C. D. (2001) Prostaglandins and leukotrienes: advances in eicosanoid biology. *Science,* 294, 1871-1875.
35. Drews, J. (2000) Drug discovery: a historical perspective. *Science,* 287, 1960-1964.
36. Lathrop, G. M. and Lalouel, J-M. (1984) Easy calculations of lod scores and genetic risks on small computers. *Am. J. Hum. Genet.,* 36, 460-465.
37. Rozen, S. and Skaletsky, H. J. (2000) Primer3 on the WWW for general users and for biologist programmers. In: Krawetz S, Misener S (eds) *Bioinformatics Methods and Protocols: Methods in Molecular Biology.* Humana Press, Totowa, N.J., pp 365-386.
38. Loden M. (2003) Role of topical emollients and moisturizers in the treatment of dry skin barrier disorders. *Am. J. Clin. Dermatol.,*4, 771-788.
39. Arseniyadis S, Subhash P V, Valleix A, Mathew S P, Blackmond D G, Wagner A, Mioskowski C. Tuning the enantioselective N-acetylation of racemic amines: a spectacular salt effect. Am Chem Soc. 2005 May 4;127(17): 6138-9.
40. Corey E J, Niwa H, Falck J R, Mioskowski C, Arai Y, Marfat A. Recent studies on the chemical synthesis of eicosanoids. Adv Prostaglandin Thromboxane Res. 1980; 6:19-25.

The invention claimed is:

1. A method of detecting the presence of, or predisposition to, the non-syndromic autosomal recessive congenital ichthyosis (ARCI) in a human subject, comprising
assessing, in a biological sample from said subject, the presence of a genetic alteration of one residue on paternal and maternal alleles of the ICHTHYIN gene, wherein the genetic alteration is selected from 247C->T, 239G->T, 341C->A, 437C->T, 523C->G and 703G->A in SEQ ID NO: 1 and
detecting the presence of, or predisposition to, the non-syndromic autosomal recessive congenital ichthyosis (ARCI) in said subject when the presence of an aforementioned genetic alteration is detected on paternal and maternal alleles of said gene.

2. The method of claim 1, wherein the biological sample comprises a tissue, cell or fluid that contains a ICHTHYIN gene.

3. The method of claim 2, wherein the biological sample comprises genomic DNA from the human subject.

* * * * *

SEQUENCE LISTING

<160> NUMBER OF SEQ ID NOS: 83

<210> SEQ ID NO 1
<211> LENGTH: 1215
<212> TYPE: DNA
<213> ORGANISM: Homo sapiens
<220> FEATURE:
<221> NAME/KEY: CDS
<222> LOCATION: (1)..(1215)
<223> OTHER INFORMATION: Homo sapiens

<400> SEQUENCE: 1

```
atg gag ctg cgg gtc agc aac acc agc tgc gag aac ggt tcc ctg ctc      48
Met Glu Leu Arg Val Ser Asn Thr Ser Cys Glu Asn Gly Ser Leu Leu
 1               5                  10                  15 cac ctc tac tgc tcc tcc caa gaa gtc ctg tgc cag att gtc aat gac      96
His Leu Tyr Cys Ser Ser Gln Glu Val Leu Cys Gln Ile Val Asn Asp
                20                  25                  30 ctc agc cct gag gtg ccc agc aat gcc acc ttt cac agc tgg cag gaa     144
Leu Ser Pro Glu Val Pro Ser Asn Ala Thr Phe His Ser Trp Gln Glu
            35                  40                  45 aga atc agg cag aac tat ggc ttc tac atc ggc ctg ggc ctg gca ttc     192
Arg Ile Arg Gln Asn Tyr Gly Phe Tyr Ile Gly Leu Gly Leu Ala Phe
        50                  55                  60 ctg tct agc ttc ctc atc ggc agc agc gtc atc ctc aag aag aaa ggc     240
Leu Ser Ser Phe Leu Ile Gly Ser Ser Val Ile Leu Lys Lys Lys Gly
65                  70                  75                  80 ctc ttg cga ctc gtg gcc acg gga gcc act cga gct gtg gat gga ggc     288
Leu Leu Arg Leu Val Ala Thr Gly Ala Thr Arg Ala Val Asp Gly Gly
                85                  90                  95 ttc ggc tac ctg aaa gat gca atg tgg tgg gct gga ttt ctc acc atg     336
Phe Gly Tyr Leu Lys Asp Ala Met Trp Trp Ala Gly Phe Leu Thr Met
            100                 105                 110 gct gct gga gaa gtt gcc aac ttt gga gcc tac gca ttt gca cct gca     384
Ala Ala Gly Glu Val Ala Asn Phe Gly Ala Tyr Ala Phe Ala Pro Ala
        115                 120                 125 aca gtc gtc acg cct cta gga gcg ctg agt gtc ctc ata agt gcc atc     432
Thr Val Val Thr Pro Leu Gly Ala Leu Ser Val Leu Ile Ser Ala Ile
    130                 135                 140 ctc tcc tca tat ttc ctg agg gag agt ctg aac ctg ctg ggg aag ctg     480
Leu Ser Ser Tyr Phe Leu Arg Glu Ser Leu Asn Leu Leu Gly Lys Leu
145                 150                 155                 160 ggc tgt gtg atc tgt gtg gcc gga agc aca gtg atg gta ata cat gct     528
Gly Cys Val Ile Cys Val Ala Gly Ser Thr Val Met Val Ile His Ala
                165                 170                 175 cct gag gaa gag aag gtc act acc atc atg gag atg gct tcc aag atg     576
Pro Glu Glu Glu Lys Val Thr Thr Ile Met Glu Met Ala Ser Lys Met
            180                 185                 190
```

```
aaa gac aca ggg ttc atc gtg ttt gct gtg ctt ctg ctg gtg tca tgc    624
Lys Asp Thr Gly Phe Ile Val Phe Ala Val Leu Leu Leu Val Ser Cys
        195                 200                 205 ctc atc ctc atc ttt gtc att gcc cca cgt tac ggg caa agg aat atc    672
Leu Ile Leu Ile Phe Val Ile Ala Pro Arg Tyr Gly Gln Arg Asn Ile
210                 215                 220 ctc atc tac atc atc atc tgc tct gtg atc ggg gcc ttc tct gtg gct    720
Leu Ile Tyr Ile Ile Ile Cys Ser Val Ile Gly Ala Phe Ser Val Ala
225                 230                 235                 240 gct gtc aag ggg ctg ggc atc acc atc aag aac ttc ttc cag ggg ctg    768
Ala Val Lys Gly Leu Gly Ile Thr Ile Lys Asn Phe Phe Gln Gly Leu
            245                 250                 255 cca gtt gtc cgg cac ccg ctc ccc tac atc ctg tcc ctc atc ctg gca    816
Pro Val Val Arg His Pro Leu Pro Tyr Ile Leu Ser Leu Ile Leu Ala
        260                 265                 270 ctg tcc ctc agc act cag gtc aac ttc ctc aac aga gca ctg gac att    864
Leu Ser Leu Ser Thr Gln Val Asn Phe Leu Asn Arg Ala Leu Asp Ile
    275                 280                 285 ttc aac act tcc ctg gtg ttc ccc atc tac tac gtg ttc ttc acc acg    912
Phe Asn Thr Ser Leu Val Phe Pro Ile Tyr Tyr Val Phe Phe Thr Thr
290                 295                 300 gtg gtc gtt acc tcg tcc atc atc ctc ttc aag gag tgg tac agc atg    960
Val Val Val Thr Ser Ser Ile Ile Leu Phe Lys Glu Trp Tyr Ser Met
305                 310                 315                 320 tct gct gtg gac att gca ggc acc ctc tcg ggc ttt gtc acc atc atc    1008
Ser Ala Val Asp Ile Ala Gly Thr Leu Ser Gly Phe Val Thr Ile Ile
            325                 330                 335 ttg ggc gtg ttc atg ctg cat gct ttc aaa gac ctg gac atc agc tgc    1056
Leu Gly Val Phe Met Leu His Ala Phe Lys Asp Leu Asp Ile Ser Cys
        340                 345                 350 gcc agc ttg ccc cac atg cac aaa aac cca ccc cct tct ccc gcc ccg    1104
Ala Ser Leu Pro His Met His Lys Asn Pro Pro Pro Ser Pro Ala Pro
    355                 360                 365 gaa ccc act gtc att aga ctg gaa gac aag aac gtc ctt gtg gac aat    1152
Glu Pro Thr Val Ile Arg Leu Glu Asp Lys Asn Val Leu Val Asp Asn
370                 375                 380 ata gaa ctt gcc agc acc tca tca cca gaa gag aaa ccc aaa gta ttt    1200
Ile Glu Leu Ala Ser Thr Ser Ser Pro Glu Glu Lys Pro Lys Val Phe
385                 390                 395                 400 ata atc cat tcc tga                                                 1215
Ile Ile His Ser <210> SEQ ID NO 2
<211> LENGTH: 404
<212> TYPE: PRT
<213> ORGANISM: Homo sapiens

<400> SEQUENCE: 2

Met Glu Leu Arg Val Ser Asn Thr Ser Cys Glu Asn Gly Ser Leu Leu
1               5                   10                  15

His Leu Tyr Cys Ser Ser Gln Glu Val Leu Cys Gln Ile Val Asn Asp
            20                  25                  30

Leu Ser Pro Glu Val Pro Ser Asn Ala Thr Phe His Ser Trp Gln Glu
        35                  40                  45

Arg Ile Arg Gln Asn Tyr Gly Phe Tyr Ile Gly Leu Gly Leu Ala Phe
    50                  55                  60

Leu Ser Ser Phe Leu Ile Gly Ser Ser Val Ile Leu Lys Lys Lys Gly
65                  70                  75                  80
```

```
Leu Leu Arg Leu Val Ala Thr Gly Ala Thr Arg Ala Val Asp Gly Gly
                85                  90                  95

Phe Gly Tyr Leu Lys Asp Ala Met Trp Trp Ala Gly Phe Leu Thr Met
            100                 105                 110

Ala Ala Gly Glu Val Ala Asn Phe Gly Ala Tyr Ala Phe Ala Pro Ala
        115                 120                 125

Thr Val Val Thr Pro Leu Gly Ala Leu Ser Val Leu Ile Ser Ala Ile
130                 135                 140

Leu Ser Ser Tyr Phe Leu Arg Glu Ser Leu Asn Leu Leu Gly Lys Leu
145                 150                 155                 160

Gly Cys Val Ile Cys Val Ala Gly Ser Thr Val Met Val Ile His Ala
                165                 170                 175

Pro Glu Glu Glu Lys Val Thr Thr Ile Met Glu Met Ala Ser Lys Met
            180                 185                 190

Lys Asp Thr Gly Phe Ile Val Phe Ala Val Leu Leu Leu Val Ser Cys
        195                 200                 205

Leu Ile Leu Ile Phe Val Ile Ala Pro Arg Tyr Gly Gln Arg Asn Ile
210                 215                 220

Leu Ile Tyr Ile Ile Ile Cys Ser Val Ile Gly Ala Phe Ser Val Ala
225                 230                 235                 240

Ala Val Lys Gly Leu Gly Ile Thr Ile Lys Asn Phe Phe Gln Gly Leu
                245                 250                 255

Pro Val Val Arg His Pro Leu Pro Tyr Ile Leu Ser Leu Ile Leu Ala
            260                 265                 270

Leu Ser Leu Ser Thr Gln Val Asn Phe Leu Asn Arg Ala Leu Asp Ile
        275                 280                 285

Phe Asn Thr Ser Leu Val Phe Pro Ile Tyr Tyr Val Phe Phe Thr Thr
290                 295                 300

Val Val Val Thr Ser Ser Ile Ile Leu Phe Lys Glu Trp Tyr Ser Met
305                 310                 315                 320

Ser Ala Val Asp Ile Ala Gly Thr Leu Ser Gly Phe Val Thr Ile Ile
                325                 330                 335

Leu Gly Val Phe Met Leu His Ala Phe Lys Asp Leu Asp Ile Ser Cys
            340                 345                 350

Ala Ser Leu Pro His Met His Lys Asn Pro Pro Ser Pro Ala Pro
        355                 360                 365

Glu Pro Thr Val Ile Arg Leu Glu Asp Lys Asn Val Leu Val Asp Asn
        370                 375                 380

Ile Glu Leu Ala Ser Thr Ser Ser Pro Glu Glu Lys Pro Lys Val Phe
385                 390                 395                 400

Ile Ile His Ser

<210> SEQ ID NO 3
<211> LENGTH: 17
<212> TYPE: DNA
<213> ORGANISM: artificial sequence
<220> FEATURE:
<223> OTHER INFORMATION: primer

<400> SEQUENCE: 3
gccacgcggg ggacaat                                                  17

<210> SEQ ID NO 4
<211> LENGTH: 20
<212> TYPE: DNA
<213> ORGANISM: artificial sequence
```

```
<220> FEATURE:
<223> OTHER INFORMATION: primer

<400> SEQUENCE: 4
cctgcaggca ctgatgtaaa                                              20

<210> SEQ ID NO 5
<211> LENGTH: 18
<212> TYPE: DNA
<213> ORGANISM: artificial sequence
<220> FEATURE:
<223> OTHER INFORMATION: primer

<400> SEQUENCE: 5
gacaagtcgc ggccacct                                                18

<210> SEQ ID NO 6
<211> LENGTH: 22
<212> TYPE: DNA
<213> ORGANISM: artificial sequence
<220> FEATURE:
<223> OTHER INFORMATION: primer

<400> SEQUENCE: 6
ctcaagaaaa gagagcccat tg                                           22

<210> SEQ ID NO 7
<211> LENGTH: 18
<212> TYPE: DNA
<213> ORGANISM: artificial sequence
<220> FEATURE:
<223> OTHER INFORMATION: primer

<400> SEQUENCE: 7
acaagtcgcg gccacctg                                                18

<210> SEQ ID NO 8
<211> LENGTH: 21
<212> TYPE: DNA
<213> ORGANISM: artificial sequence
<220> FEATURE:
<223> OTHER INFORMATION: primer

<400> SEQUENCE: 8
caggaagttc tgccaccatt g                                            21

<210> SEQ ID NO 9
<211> LENGTH: 17
<212> TYPE: PRT
<213> ORGANISM: artificial sequence
<220> FEATURE:
<223> OTHER INFORMATION: C-17-K peptide

<400> SEQUENCE: 9

Cys Asp Asn Ile Glu Leu Ala Ser Thr Ser Ser Pro Glu Glu Lys Pro
1               5                   10                  15

Lys

<210> SEQ ID NO 10
<211> LENGTH: 19
<212> TYPE: DNA
<213> ORGANISM: artificial sequence
<220> FEATURE:
<223> OTHER INFORMATION: primer

<400> SEQUENCE: 10
```
ctcacctctt gccctagc                                                19

<210> SEQ ID NO 11
<211> LENGTH: 20
<212> TYPE: DNA
<213> ORGANISM: artificial sequence
<220> FEATURE:
<223> OTHER INFORMATION: primer

<400> SEQUENCE: 11
gccagaaccc agatcttcaa                                              20

<210> SEQ ID NO 12
<211> LENGTH: 20
<212> TYPE: DNA
<213> ORGANISM: artificial sequence
<220> FEATURE:
<223> OTHER INFORMATION: primer

<400> SEQUENCE: 12
ttatctggca cgtggtggta                                              20

<210> SEQ ID NO 13
<211> LENGTH: 20
<212> TYPE: DNA
<213> ORGANISM: artificial sequence
<220> FEATURE:
<223> OTHER INFORMATION: primer

<400> SEQUENCE: 13
aggtgggatt ccagataggg                                              20

<210> SEQ ID NO 14
<211> LENGTH: 20
<212> TYPE: DNA
<213> ORGANISM: artificial sequence
<220> FEATURE:
<223> OTHER INFORMATION: primer

<400> SEQUENCE: 14
gcctgtgagg aatccaagag                                              20

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
ctgggcctca gattcacact                                              20

<210> SEQ ID NO 16
<211> LENGTH: 20
<212> TYPE: DNA
<213> ORGANISM: artificial sequence
<220> FEATURE:
<223> OTHER INFORMATION: primer

<400> SEQUENCE: 16
ctccagggag agagcgtatg                                              20

<210> SEQ ID NO 17
<211> LENGTH: 20
<212> TYPE: DNA

```
<213> ORGANISM: artificial sequence
<220> FEATURE:
<223> OTHER INFORMATION: primer

<400> SEQUENCE: 17
ggcctgcctc tctattaccc                                                    20

<210> SEQ ID NO 18
<211> LENGTH: 20
<212> TYPE: DNA
<213> ORGANISM: artificial sequence
<220> FEATURE:
<223> OTHER INFORMATION: primer

<400> SEQUENCE: 18
gaacaatgtc tcccgtggat                                                    20

<210> SEQ ID NO 19
<211> LENGTH: 21
<212> TYPE: DNA
<213> ORGANISM: artificial sequence
<220> FEATURE:
<223> OTHER INFORMATION: primer

<400> SEQUENCE: 19
ccatacatat caggccagga a                                                  21

<210> SEQ ID NO 20
<211> LENGTH: 22
<212> TYPE: DNA
<213> ORGANISM: artificial sequence
<220> FEATURE:
<223> OTHER INFORMATION: primer

<400> SEQUENCE: 20
ttgggggttt aaaaacctaa cc                                                 22

<210> SEQ ID NO 21
<211> LENGTH: 22
<212> TYPE: DNA
<213> ORGANISM: artificial sequence
<220> FEATURE:
<223> OTHER INFORMATION: primer

<400> SEQUENCE: 21
cagttgcact ggaaaataac ca                                                 22

<210> SEQ ID NO 22
<211> LENGTH: 22
<212> TYPE: DNA
<213> ORGANISM: artificial sequence
<220> FEATURE:
<223> OTHER INFORMATION: primer

<400> SEQUENCE: 22
gggcaaagga atatcctcat ct                                                 22

<210> SEQ ID NO 23
<211> LENGTH: 22
<212> TYPE: DNA
<213> ORGANISM: artificial sequence
<220> FEATURE:
<223> OTHER INFORMATION: primer

<400> SEQUENCE: 23
aagaggaagt gacaaaggca ac                                                 22
```

<210> SEQ ID NO 24
<211> LENGTH: 20
<212> TYPE: DNA
<213> ORGANISM: artificial sequence
<220> FEATURE:
<223> OTHER INFORMATION: primer

<400> SEQUENCE: 24
ccacgcgggg gacaagtcgc                                          20

<210> SEQ ID NO 25
<211> LENGTH: 27
<212> TYPE: DNA
<213> ORGANISM: artificial sequence
<220> FEATURE:
<223> OTHER INFORMATION: primer

<400> SEQUENCE: 25
gcaggtgcaa atgcgtaggc tccaaag                                  27

<210> SEQ ID NO 26
<211> LENGTH: 20
<212> TYPE: DNA
<213> ORGANISM: artificial sequence
<220> FEATURE:
<223> OTHER INFORMATION: primer

<400> SEQUENCE: 26
cgtcggttcg tgtgccccgg                                          20

<210> SEQ ID NO 27
<211> LENGTH: 27
<212> TYPE: DNA
<213> ORGANISM: artificial sequence
<220> FEATURE:
<223> OTHER INFORMATION: primer

<400> SEQUENCE: 27
gcaggtgcaa atgcgtaggc tccaaag                                  27

<210> SEQ ID NO 28
<211> LENGTH: 23
<212> TYPE: DNA
<213> ORGANISM: artificial sequence
<220> FEATURE:
<223> OTHER INFORMATION: primer

<400> SEQUENCE: 28
ctttggagcc tacgcatttg cac                                      23

<210> SEQ ID NO 29
<211> LENGTH: 23
<212> TYPE: DNA
<213> ORGANISM: artificial sequence
<220> FEATURE:
<223> OTHER INFORMATION: primer

<400> SEQUENCE: 29
ggacgaggta acgaccaccg tgg                                      23

<210> SEQ ID NO 30
<211> LENGTH: 18
<212> TYPE: DNA
<213> ORGANISM: artificial sequence
<220> FEATURE:

-continued

<223> OTHER INFORMATION: primer

<400> SEQUENCE: 30
caggctggga gcacctac                                                18

<210> SEQ ID NO 31
<211> LENGTH: 20
<212> TYPE: DNA
<213> ORGANISM: artificial sequence
<220> FEATURE:
<223> OTHER INFORMATION: primer

<400> SEQUENCE: 31
gggtgtcttc ctgagagctg                                              20

<210> SEQ ID NO 32
<211> LENGTH: 20
<212> TYPE: DNA
<213> ORGANISM: artificial sequence
<220> FEATURE:
<223> OTHER INFORMATION: primer

<400> SEQUENCE: 32
ccaaacctac cctgggaaat                                              20

<210> SEQ ID NO 33
<211> LENGTH: 20
<212> TYPE: DNA
<213> ORGANISM: artificial sequence
<220> FEATURE:
<223> OTHER INFORMATION: primer

<400> SEQUENCE: 33
atgcactcca gcctgaatta                                              20

<210> SEQ ID NO 34
<211> LENGTH: 20
<212> TYPE: DNA
<213> ORGANISM: artificial sequence
<220> FEATURE:
<223> OTHER INFORMATION: primer

<400> SEQUENCE: 34
gcattcccct catagctcag                                              20

<210> SEQ ID NO 35
<211> LENGTH: 20
<212> TYPE: DNA
<213> ORGANISM: artificial sequence
<220> FEATURE:
<223> OTHER INFORMATION: primer

<400> SEQUENCE: 35
catgacaatg gatcgctgaa                                              20

<210> SEQ ID NO 36
<211> LENGTH: 20
<212> TYPE: DNA
<213> ORGANISM: artificial sequence
<220> FEATURE:
<223> OTHER INFORMATION: primer

<400> SEQUENCE: 36
ccacatatcc tcagccacag                                              20

```
<210> SEQ ID NO 37
<211> LENGTH: 20
<212> TYPE: DNA
<213> ORGANISM: artificial sequence
<220> FEATURE:
<223> OTHER INFORMATION: primer

<400> SEQUENCE: 37
agatggcagc tccaagacag                                              20

<210> SEQ ID NO 38
<211> LENGTH: 20
<212> TYPE: DNA
<213> ORGANISM: artificial sequence
<220> FEATURE:
<223> OTHER INFORMATION: primer

<400> SEQUENCE: 38
aatgtggacg ctatccaagg                                              20

<210> SEQ ID NO 39
<211> LENGTH: 20
<212> TYPE: DNA
<213> ORGANISM: artificial sequence
<220> FEATURE:
<223> OTHER INFORMATION: primer

<400> SEQUENCE: 39
gggtgcttct gttgctgact                                              20

<210> SEQ ID NO 40
<211> LENGTH: 19
<212> TYPE: DNA
<213> ORGANISM: artificial sequence
<220> FEATURE:
<223> OTHER INFORMATION: primer

<400> SEQUENCE: 40
acgttcgagc tctgggtct                                               19

<210> SEQ ID NO 41
<211> LENGTH: 24
<212> TYPE: DNA
<213> ORGANISM: artificial sequence
<220> FEATURE:
<223> OTHER INFORMATION: primer

<400> SEQUENCE: 41
aaccatgaga aaggagtaga atgc                                         24

<210> SEQ ID NO 42
<211> LENGTH: 20
<212> TYPE: DNA
<213> ORGANISM: artificial sequence
<220> FEATURE:
<223> OTHER INFORMATION: primer

<400> SEQUENCE: 42
gcaacaaggc cactgcttac                                              20

<210> SEQ ID NO 43
<211> LENGTH: 20
<212> TYPE: DNA
<213> ORGANISM: artificial sequence
<220> FEATURE:
<223> OTHER INFORMATION: primer
```

```
<400> SEQUENCE: 43
ggctgaggac aagctacagg                                              20

<210> SEQ ID NO 44
<211> LENGTH: 20
<212> TYPE: DNA
<213> ORGANISM: artificial sequence
<220> FEATURE:
<223> OTHER INFORMATION: primer

<400> SEQUENCE: 44
tgactgctga ttggaaatgc                                              20

<210> SEQ ID NO 45
<211> LENGTH: 22
<212> TYPE: DNA
<213> ORGANISM: artificial sequence
<220> FEATURE:
<223> OTHER INFORMATION: primer

<400> SEQUENCE: 45
aacctctcct ggaagattgt ca                                           22

<210> SEQ ID NO 46
<211> LENGTH: 20
<212> TYPE: DNA
<213> ORGANISM: artificial sequence
<220> FEATURE:
<223> OTHER INFORMATION: primer

<400> SEQUENCE: 46
agaatgtgtg gcatgcaaat                                              20

<210> SEQ ID NO 47
<211> LENGTH: 22
<212> TYPE: DNA
<213> ORGANISM: artificial sequence
<220> FEATURE:
<223> OTHER INFORMATION: primer

<400> SEQUENCE: 47
aggagctcag gaaactgatg tt                                           22

<210> SEQ ID NO 48
<211> LENGTH: 22
<212> TYPE: DNA
<213> ORGANISM: artificial sequence
<220> FEATURE:
<223> OTHER INFORMATION: primer

<400> SEQUENCE: 48
ccatgagaaa ctggaagaac aa                                           22

<210> SEQ ID NO 49
<211> LENGTH: 23
<212> TYPE: DNA
<213> ORGANISM: artificial sequence
<220> FEATURE:
<223> OTHER INFORMATION: primer

<400> SEQUENCE: 49
cactgaaaat agcacctttg gtt                                          23

<210> SEQ ID NO 50
<211> LENGTH: 20
```

```
<212> TYPE: DNA
<213> ORGANISM: artificial sequence
<220> FEATURE:
<223> OTHER INFORMATION: primer

<400> SEQUENCE: 50
ctgcaccgag cctgattatt                                          20

<210> SEQ ID NO 51
<211> LENGTH: 20
<212> TYPE: DNA
<213> ORGANISM: artificial sequence
<220> FEATURE:
<223> OTHER INFORMATION: primer

<400> SEQUENCE: 51
tgaaacgcca tgtctgtagc                                          20

<210> SEQ ID NO 52
<211> LENGTH: 23
<212> TYPE: DNA
<213> ORGANISM: artificial sequence
<220> FEATURE:
<223> OTHER INFORMATION: primer

<400> SEQUENCE: 52
cttctcttta gagagtgccc aca                                      23

<210> SEQ ID NO 53
<211> LENGTH: 20
<212> TYPE: DNA
<213> ORGANISM: artificial sequence
<220> FEATURE:
<223> OTHER INFORMATION: primer

<400> SEQUENCE: 53
gtgggggaaa ggactgaaat                                          20

<210> SEQ ID NO 54
<211> LENGTH: 20
<212> TYPE: DNA
<213> ORGANISM: artificial sequence
<220> FEATURE:
<223> OTHER INFORMATION: primer

<400> SEQUENCE: 54
actggggcct tgtaaaggaa                                          20

<210> SEQ ID NO 55
<211> LENGTH: 20
<212> TYPE: DNA
<213> ORGANISM: artificial sequence
<220> FEATURE:
<223> OTHER INFORMATION: primer

<400> SEQUENCE: 55
aggaaaaccg cttcagaaca                                          20

<210> SEQ ID NO 56
<211> LENGTH: 20
<212> TYPE: DNA
<213> ORGANISM: artificial sequence
<220> FEATURE:
<223> OTHER INFORMATION: primer

<400> SEQUENCE: 56
```

-continued

```
agtaagctgc ctgtcgaagc                                              20

<210> SEQ ID NO 57
<211> LENGTH: 21
<212> TYPE: DNA
<213> ORGANISM: artificial sequence
<220> FEATURE:
<223> OTHER INFORMATION: primer

<400> SEQUENCE: 57
caagaccttg gctcagaaaa a                                            21

<210> SEQ ID NO 58
<211> LENGTH: 24
<212> TYPE: DNA
<213> ORGANISM: artificial sequence
<220> FEATURE:
<223> OTHER INFORMATION: primer

<400> SEQUENCE: 58
tgaagaaata tacaggttgg tgct                                         24

<210> SEQ ID NO 59
<211> LENGTH: 20
<212> TYPE: DNA
<213> ORGANISM: artificial sequence
<220> FEATURE:
<223> OTHER INFORMATION: primer

<400> SEQUENCE: 59
cacgaggaat gaagatgtgg                                              20

<210> SEQ ID NO 60
<211> LENGTH: 20
<212> TYPE: DNA
<213> ORGANISM: artificial sequence
<220> FEATURE:
<223> OTHER INFORMATION: primer

<400> SEQUENCE: 60
agaaatcccg agtcatgcag                                              20

<210> SEQ ID NO 61
<211> LENGTH: 20
<212> TYPE: DNA
<213> ORGANISM: artificial sequence
<220> FEATURE:
<223> OTHER INFORMATION: primer

<400> SEQUENCE: 61
agcctgggtg acagagtgag                                              20

<210> SEQ ID NO 62
<211> LENGTH: 20
<212> TYPE: DNA
<213> ORGANISM: artificial sequence
<220> FEATURE:
<223> OTHER INFORMATION: primer

<400> SEQUENCE: 62
ctgggcgaca gagtgagact                                              20

<210> SEQ ID NO 63
<211> LENGTH: 20
<212> TYPE: DNA
<213> ORGANISM: artificial sequence
```

```
<220> FEATURE:
<223> OTHER INFORMATION: primer

<400> SEQUENCE: 63
aagcgaagtt ctccaggttg                                               20

<210> SEQ ID NO 64
<211> LENGTH: 20
<212> TYPE: DNA
<213> ORGANISM: artificial sequence
<220> FEATURE:
<223> OTHER INFORMATION: primer

<400> SEQUENCE: 64
gcgaaagcca gaatcttcat                                               20

<210> SEQ ID NO 65
<211> LENGTH: 20
<212> TYPE: DNA
<213> ORGANISM: artificial sequence
<220> FEATURE:
<223> OTHER INFORMATION: primer

<400> SEQUENCE: 65
caggcttggg attgatagga                                               20

<210> SEQ ID NO 66
<211> LENGTH: 20
<212> TYPE: DNA
<213> ORGANISM: artificial sequence
<220> FEATURE:
<223> OTHER INFORMATION: primer

<400> SEQUENCE: 66
gcttgggctg caaaataaag                                               20

<210> SEQ ID NO 67
<211> LENGTH: 21
<212> TYPE: DNA
<213> ORGANISM: artificial sequence
<220> FEATURE:
<223> OTHER INFORMATION: primer

<400> SEQUENCE: 67
gacgtcttta aaggcatgca a                                             21

<210> SEQ ID NO 68
<211> LENGTH: 20
<212> TYPE: DNA
<213> ORGANISM: artificial sequence
<220> FEATURE:
<223> OTHER INFORMATION: primer

<400> SEQUENCE: 68
gagcctcatc gtctgtgtga                                               20

<210> SEQ ID NO 69
<211> LENGTH: 20
<212> TYPE: DNA
<213> ORGANISM: artificial sequence
<220> FEATURE:
<223> OTHER INFORMATION: primer

<400> SEQUENCE: 69
cgtcatgtgc tgaggtcatt                                               20
```

```
<210> SEQ ID NO 70
<211> LENGTH: 20
<212> TYPE: DNA
<213> ORGANISM: artificial sequence
<220> FEATURE:
<223> OTHER INFORMATION: primer

<400> SEQUENCE: 70
cttcagctgg cacaacaaga                                              20

<210> SEQ ID NO 71
<211> LENGTH: 20
<212> TYPE: DNA
<213> ORGANISM: artificial sequence
<220> FEATURE:
<223> OTHER INFORMATION: primer

<400> SEQUENCE: 71
tggcaccact gttgtcgtat                                              20

<210> SEQ ID NO 72
<211> LENGTH: 20
<212> TYPE: DNA
<213> ORGANISM: artificial sequence
<220> FEATURE:
<223> OTHER INFORMATION: primer

<400> SEQUENCE: 72
tgattctgct aaccctggtg                                              20

<210> SEQ ID NO 73
<211> LENGTH: 20
<212> TYPE: DNA
<213> ORGANISM: artificial sequence
<220> FEATURE:
<223> OTHER INFORMATION: primer

<400> SEQUENCE: 73
ataacaggcc aacagccatc                                              20

<210> SEQ ID NO 74
<211> LENGTH: 20
<212> TYPE: DNA
<213> ORGANISM: artificial sequence
<220> FEATURE:
<223> OTHER INFORMATION: primer

<400> SEQUENCE: 74
caaggtggcc atgcatatct                                              20

<210> SEQ ID NO 75
<211> LENGTH: 21
<212> TYPE: DNA
<213> ORGANISM: artificial sequence
<220> FEATURE:
<223> OTHER INFORMATION: primer

<400> SEQUENCE: 75
gcaacaagaa tatccccaca a                                            21

<210> SEQ ID NO 76
<211> LENGTH: 20
<212> TYPE: DNA
<213> ORGANISM: artificial sequence
<220> FEATURE:
<223> OTHER INFORMATION: primer
```

<400> SEQUENCE: 76
gagcctcatc gtctgtgtga                                                    20

<210> SEQ ID NO 77
<211> LENGTH: 20
<212> TYPE: DNA
<213> ORGANISM: artificial sequence
<220> FEATURE:
<223> OTHER INFORMATION: primer

<400> SEQUENCE: 77
cgtcatgtgc tgaggtcatt                                                    20

<210> SEQ ID NO 78
<211> LENGTH: 20
<212> TYPE: DNA
<213> ORGANISM: artificial sequence
<220> FEATURE:
<223> OTHER INFORMATION: primer

<400> SEQUENCE: 78
ggcccaagac atcttgcata                                                    20

<210> SEQ ID NO 79
<211> LENGTH: 20
<212> TYPE: DNA
<213> ORGANISM: artificial sequence
<220> FEATURE:
<223> OTHER INFORMATION: primer

<400> SEQUENCE: 79
gctatccacc agaccacctg                                                    20

<210> SEQ ID NO 80
<211> LENGTH: 20
<212> TYPE: DNA
<213> ORGANISM: artificial sequence
<220> FEATURE:
<223> OTHER INFORMATION: primer

<400> SEQUENCE: 80
gggaccctga gtggattctt                                                    20

<210> SEQ ID NO 81
<211> LENGTH: 19
<212> TYPE: DNA
<213> ORGANISM: artificial sequence
<220> FEATURE:
<223> OTHER INFORMATION: primer

<400> SEQUENCE: 81
ccacctggca gagacaaag                                                     19

<210> SEQ ID NO 82
<211> LENGTH: 20
<212> TYPE: DNA
<213> ORGANISM: artificial sequence
<220> FEATURE:
<223> OTHER INFORMATION: primer

<400> SEQUENCE: 82
ggaagaagcc cattccattt                                                    20

<210> SEQ ID NO 83

```
<211> LENGTH: 20
<212> TYPE: DNA
<213> ORGANISM: artificial sequence
<220> FEATURE:
<223> OTHER INFORMATION: primer

<400> SEQUENCE: 83
caggcagagg ctggattcta                                              20
```